United States Patent
Chen et al.

(10) Patent No.: US 12,350,374 B2
(45) Date of Patent: Jul. 8, 2025

(54) FABRICATION OF PROTEIN-ENCAPSULATING MICROGELS

(71) Applicant: Regeneron Pharmaceuticals, Inc., Tarrytown, NY (US)

(72) Inventors: Hunter Chen, New York, NY (US); Yiming Zhao, Great Neck, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 0 days.

(21) Appl. No.: 17/553,507

(22) Filed: Dec. 16, 2021

(65) Prior Publication Data

US 2022/0257707 A1  Aug. 18, 2022

Related U.S. Application Data

(60) Provisional application No. 63/127,033, filed on Dec. 17, 2020.

(51) Int. Cl.
| | | |
|---|---|---|
| *A61K 9/16* | (2006.01) | |
| *A61K 9/06* | (2006.01) | |
| *A61K 9/50* | (2006.01) | |
| *A61K 38/17* | (2006.01) | |
| *A61K 47/10* | (2017.01) | |

(52) U.S. Cl.
CPC ............ *A61K 9/1694* (2013.01); *A61K 9/06* (2013.01); *A61K 9/5089* (2013.01); *A61K 38/179* (2013.01); *A61K 47/10* (2013.01)

(58) Field of Classification Search
CPC ...... A61K 38/179; A61K 9/06; A61K 9/5089; A61K 47/10; C07K 16/10
See application file for complete search history.

(56) References Cited

U.S. PATENT DOCUMENTS

2020/0038328 A1   2/2020   Chen et al.

FOREIGN PATENT DOCUMENTS

WO   2009073193 A2   6/2009

OTHER PUBLICATIONS

Mana et al: "Oil-in-oil microencapsulation technique with an external perfluorohexane phase", International Journal of Pharmaceutics, Elsevier, NL, vol. 338, No. 1-2, May 23, 2007 (May 23, 2007), pp. 231-237.
Uchida T et al: "Microencapsulation of Ovalbumin in Poly(Lactide-Co-Glycolide) By an Oil-In-Oil (0/0) Solvent Evaporation Method", Journal of Microencapsulation, Taylor and Francis, Basingstoke, GB, vol. 13, No. 5, Sep. 1, 1996 (Sep. 1, 19961), pp. 509-518.
International Search Report, International Application No. PCT/US2021/063890, International Filing Date Dec. 16, 2021, Mailing Date Apr. 7, 2022.

*Primary Examiner* — Robert A Wax
*Assistant Examiner* — Olga V. Tcherkasskaya
(74) *Attorney, Agent, or Firm* — BakerHostetler

(57) ABSTRACT

The present invention provides methods for fabricating protein-encapsulating microgels using hydrocarbon-in-fluorocarbon emulsions. The non-aqueous emulsion-based microgel fabrication methods can be used for the encapsulation of a wide range of proteins and peptides, including antibodies and antibody-fusion proteins, for therapeutic use with ease of administration.

17 Claims, 6 Drawing Sheets

Pico-Surf 1 (PFPE-PEG-PFPE)

Figure 3.
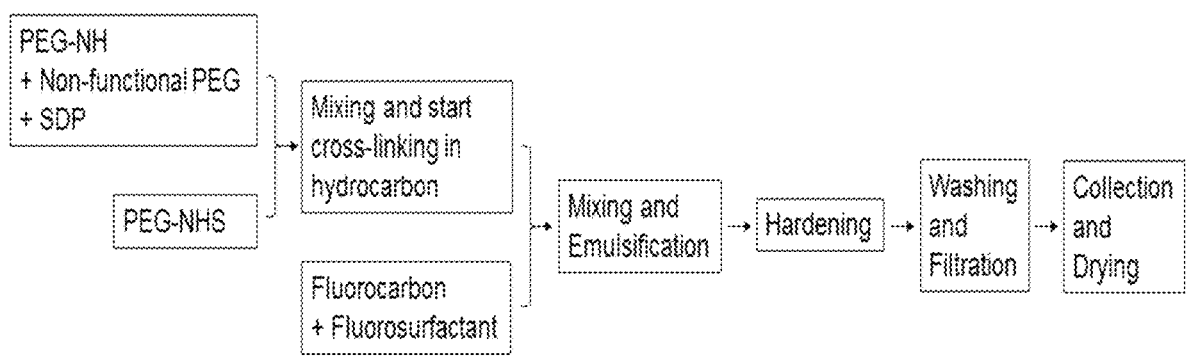
Figure 4A.         Figure 4B.
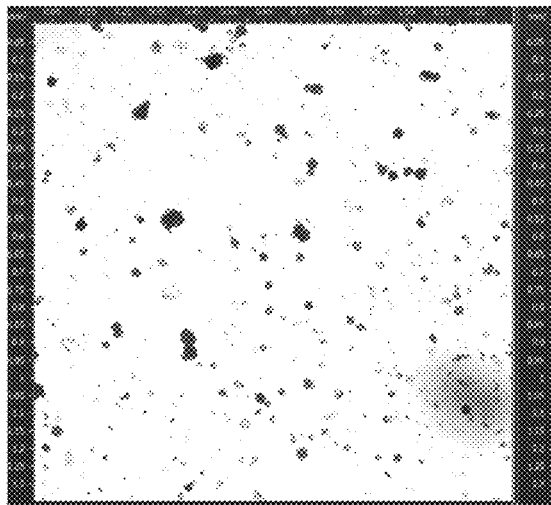 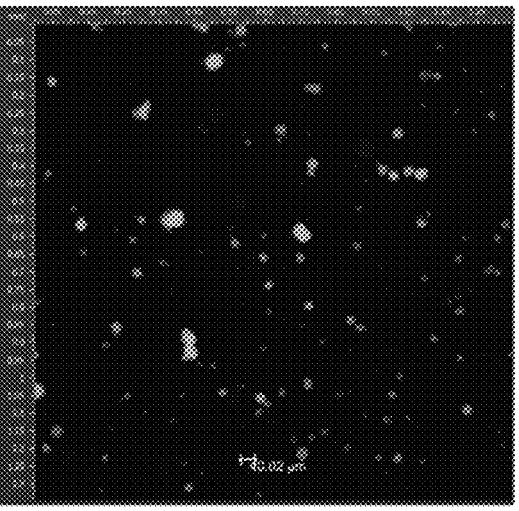

Figure 5A
Figure 5B
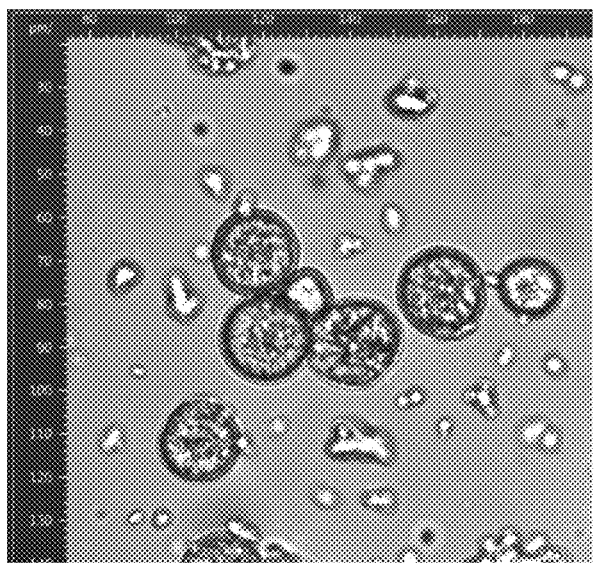
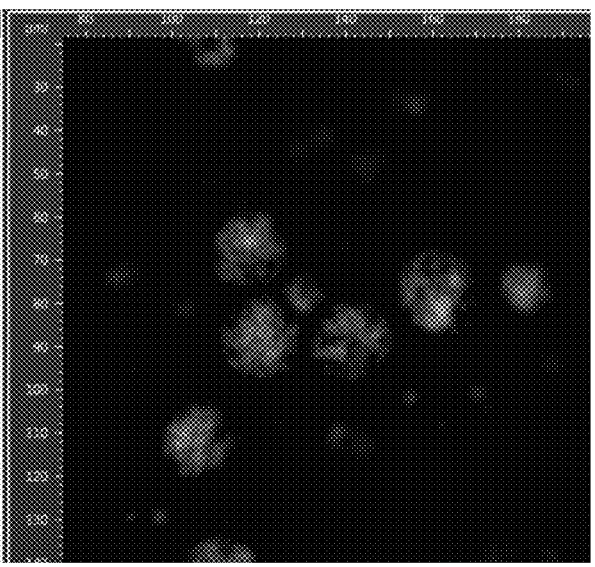

Figure 6A
Figure 6B
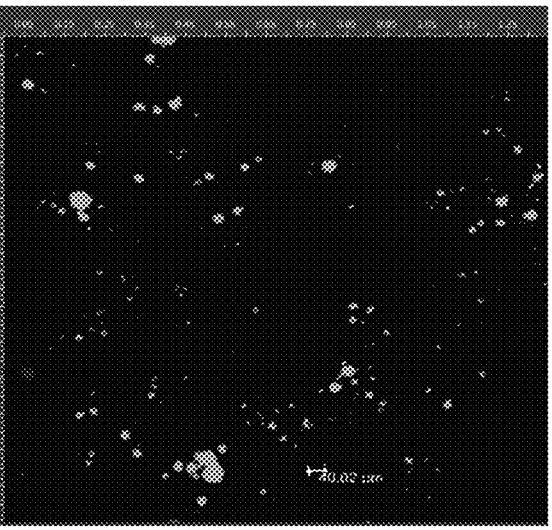

ated to and the benefit of U.S.

FABRICATION OF PROTEIN-ENCAPSULATING MICROGELS

CROSS-REFERENCE TO RELATED APPLICATIONS

This application claims priority to and the benefit of U.S. Provisional Patent Application No. 63/127,033, filed Dec. 17, 2020 which is herein incorporated by reference.

FIELD

The present invention generally pertains to drug microgels, formulations containing drug microgels, and methods of making drug microgels using non-aqueous emulsion systems.

BACKGROUND

The extended or sustained release delivery of a therapeutic protein toward a biologically relevant target is desirable for the treatment of medical conditions, such as cancer, cardiovascular disease, vascular conditions, orthopedic disorders, dental disorders, wounds, autoimmune disease, gastrointestinal disorders, and ocular diseases because it permits larger dosages which require less frequent administration. Reducing the number of injections or prolongation of injection interval can be desirable for patient compliance, especially where a doctor is required to do the injection, such as in the case of intraocular therapeutics.

Biocompatible and biodegradable polymers and other implantable delivery devices for the controlled and sustained delivery of drugs have been in use, including, for example, polymer-based delivery devices where the polymer degrades over time and the therapeutic drug is slowly released. There are, however, various challenges in maintaining a drug's stability when using polymers and polymer-based delivery devices, especially for delivery of protein therapeutics.

Therapeutic macromolecules, such as antibodies and receptor Fc-fusion proteins, must be formulated in a manner that not only makes the molecules suitable for administration to patients, but also maintains their stability during storage and while at the site of administration. For example, therapeutic proteins (such as antibodies or fusion proteins) in aqueous solution are prone to degradation, aggregation, and/or undesired chemical modifications unless the solution is formulated properly.

When formulating a therapeutic protein for sustained release, great care must be taken to arrive at a formulation that remains stable over time, at storage and physiological temperature, contains an adequate concentration of the therapeutic protein (for example, antibody), and possesses other properties that enable the formulation to be conveniently administered to patients.

Some extended or sustained release formulations are produced using encapsulation methodologies that include formation of multiple emulsions, internal phase separation, interfacial polymerization, layer-by-layer adsorption of polyelectrolytes, and soft templating techniques. For example, the most common type of multiple emulsions is water-in-oil-in-water (W/O/W). Multiple emulsions in W/O/W enables the encapsulation of aqueous/hydrophilic cores directly in aqueous suspension; however, there specific problems when used to encapsulate biologically active agents into extended or sustained release formulations. For example, precipitation of proteins may occur at the aqueous organic interface with concomitant reduction in the protein's immunoreactivity.

In other aqueous emulsion systems, water can diffuse into the organic phase and hydrolyze the protein. After hydrolysis, protein droplets start to merge and escape into the aqueous environment and aggregate or precipitate. After hardening, voids and water channels may appear where protein once was but escaped into the aqueous environment.

In another example, hydrogel microparticles (referred to herein as "microgels") may be used to provide extended or sustained release formulations of therapeutic proteins. Microgels are microstructures that may comprise crosslinked hydrophilic polymeric networks hydrated by large amounts of water. The crosslinks connecting the polymers may be formed using a covalent, ionic, affinity, and/or physical basis. Microgels, in contrast to bulk hydrogels that require surgery to implant, are soft, deformable and can be administered with a needle or catheter, which is less invasive and can lead to better therapeutic outcomes.

Several synthesis routes are available for the fabrication of microgels. Batch emulsion or precipitation polymerization are currently the most common methods based on water-in-oil emulsions or inversed oil-in-water emulsions. In these methods, the presence of the aqueous phase limits the encapsulation efficiency of hydrophilic payloads.

Although many immiscible solvent pairs are available to choose from in the fabrication of microgels, normally one polar and one non-polar solvent are selected. It can be a challenge to find a pair that is suitable for synthesis of polymer microgels (sometimes referred to herein as microspheres), however, because typical biodegradable polymers, including, for example, poly(lactide-co-glycolide) (PLGA), polylactic acid (PLA), or poly(ortho ester) (POE), are mostly soluble in solvents with medium polarity such as chloroform, dichloromethane, or ethyl acetate. This limits the selection of the continuous phase. In addition, compatibility with process, toxicity, safety, and residual solvents are concerns of using those organic solvents and should be considered for use as a pharmaceutical product.

Other fabrication methods like lithography, microfluidic polymerization, and electrospraying are typically used as small lab-scale methods and may experience challenges when scaling-up in a clinical or commercial manufacturing setting. Various kinds of emulsion systems containing fluorocarbons have been fabricated through microfluidics methods, such as water-in-fluorocarbon (W/F), water-in-fluorocarbon-in-water (W/F/W) double emulsion, water/fluorocarbon/oil/water (W/F/O/W) triple emulsion, fluorocarbon/hydrocarbon/water (F/H/W) double emulsion, and hydrocarbon/fluorocarbon/water (H/F/W) double emulsion. Some of these emulsions have been used for synthesis of polymeric microspheres. However, all of them are still aqueous-based emulsion systems, using water as a dispersed or continuous phase.

Thus, there exists a need for methods for producing microgels using non-aqueous emulsion systems.

Thus, there is an unmet need for improved polymers and polymer-based delivery devices that provide extended or sustained release formulations to deliver drugs effectively over time with as few injections as possible. In the case of other diseases, for example cancer and diseases of inflammation, there is a need for improved implantable extended or sustained release formulations containing stable and effective protein therapeutics.

Therefore, it would be desirable to provide non-aqueous emulsion systems to produce drug formulations and methods of their use. It would also be desirable to provide extended release formulations with improved protein stability, stable extended or sustained release (sustained release), and ease of administration.

Non-aqueous emulsions can replace conventional aqueous emulsions wherever the presence of water is undesirable. Two types of hydrocarbon-based non-aqueous emulsion systems are: (1) two immiscible organic solvents, stabilized by blocking copolymers (for example, hexane/dimethylformamide); and (2) oil-immiscible polar solvents (for example formamide, acetonitrile) replacing water using existing surfactants. Water-in-perfluorinated oil (W/F) emulsions have been applied in droplet-based microfluidics for single-cell or single-molecule biological assays, with perfluoropolyether-b-polyethylene glycol-b-perfluoropolyether (PFPE-PEG-PFPE) used as a fluorosurfactant (FS) for stabilizing water droplets in fluorocarbon solvents.

Accordingly, some embodiments in accordance with the present invention use fluorocarbons as the continuous phase in a non-aqueous emulsion system because they have several desirable properties. Firstly, fluorocarbons are neither hydrophobic nor hydrophilic: they are immiscible with most organic (hydrocarbon) solvents, making them ideal as the continuous phase for hydrocarbon droplet emulsions. Secondly, fluorocarbons are non-solvents for proteins and other hydrophilic molecules, hydrocarbon-based polymers, and organic excipients; in other words, these types of molecules will not be soluble in fluorocarbon. Thirdly, fluorocarbons have low viscosity. Fourth, fluorocarbons are chemically inert and can be relatively less toxic or corrosive compared to commonly used hydrocarbon solvents. Finally, fluorocarbons are volatile and recyclable.

SUMMARY

A method has been developed for producing microgels using non-aqueous emulsion systems. The method includes combining at least one biodegradable and/or bioerodible cross-linkable polymer and at least one cross-linking modulator with a hydrocarbon solvent to form a non-aqueous first solution or dispersed phase suspension. The first solution or dispersed phase suspension is added to a second solution, or continuous phase solution, containing a fluorocarbon liquid and a fluorosurfactant. The solution mixture is emulsified through an emulsification method. By first removing the hydrocarbon solvent and then the fluorocarbon liquid, a powder of microgel particles can be recovered. By suspending a powder including a therapeutic active agent, for example a therapeutic protein, in the dispersed phase suspension, a slow-release or sustained-release therapeutic or drug microparticle may be produced.

In some exemplary embodiments, drug microparticles provided in accordance with the present disclosure include an active ingredient (such as, for example, a protein) surrounded by a cross-linked polymer microgel cortex. Drug microparticles produced by the disclosed methods may have a cross-linked polymer microgel cortex that is devoid of pores or channels, and not perforated. In some exemplary embodiments, the drug microparticles may have a diameter between about 1 μm and about 200 μm.

The drug microparticles are prepared in accordance with the present disclosure using non-aqueous emulsion systems by combining the active ingredient (for example, a dry protein powder), one or more biodegradable and/or a bioerodible crosslinkable polymers or polymer precursors, and a cross-linking modulator, into a hydrocarbon solvent to form a non-aqueous first solution or dispersed phase suspension, and adding the first solution or dispersed phase suspension to a second solution or continuous phase solution comprising a fluorocarbon liquid and a fluorosurfactant. The solution mixture is emulsified through an emulsification method. By first removing the hydrocarbon solvent and then fluorocarbon liquid, the drug microparticles can be recovered.

Formulations containing the drug microparticles are also provided in accordance with the present disclosure.

In particular aspects, the present disclosure relates to a method of producing microparticles including the steps of combining an active ingredient (e.g., a dry protein powder) and one or more crosslinkable polymer precursors with a hydrocarbon solvent to form a non-aqueous first solution.

The method further includes adding the first solution to a second solution, wherein the second solution comprises a fluorocarbon liquid and a fluorosurfactant. The method further includes agitating the combined first and second solutions to form a non-aqueous emulsion having multiple emulsion hydrocarbon droplets in the fluorocarbon liquid. The method further includes removing the hydrocarbon solvent and removing the fluorocarbon liquid to isolate the microgels, wherein the microgels include the active ingredient encapsulated within a matrix of crosslinked polymer.

In exemplary embodiments, the second solution may contain a perfluoro C5-C18 compound. In other embodiments, the second solution may contain perfluorotripentylamine, sold under the trademark Fluorinert™ FC-70. The active ingredient (e.g., a dry protein powder) and one or more crosslinkable polymer precursors may be combined with a hydrocarbon solvent selected from dichloromethane, chloroform, toluene, ethyl acetate, tetrahydrofuran, or a combination thereof. In yet other embodiments, the active ingredient and one or more crosslinkable polymer precursors is combined with a hydrocarbon solvent selected from dichloromethane, ethyl acetate, or a combination thereof.

In exemplary embodiments, the step of adding the first solution to a second solution includes adding the first solution to a second solution containing perfluoropolyether-b-polyethylene glycol-b-perfluoropolyether.

In other embodiments, the one or more cross linkable polymer precursors combined with a hydrocarbon solvent includes a core selected from polyethylene glycol, polyethylene oxide, polyethylene oxide-co-polypropylene oxide, co-polyethylene oxide block or random copolymers, polyvinyl alcohol, poly(vinyl pyrrolidinone), poly(amino acids), dextran, or any combination thereof.

In exemplary embodiments, the one or more crosslinkable polymer precursors combined with a hydrocarbon solvent includes a first crosslinkable polymer precursor including nucleophilic functional groups, and a second crosslinkable polymer precursor including electrophilic functional groups. The one or more crosslinkable polymer precursors combined with a hydrocarbon solvent may include a polyethylene glycol-amine (PEG-NH) first precursor, and a polyethylene glycol-N-hydroxysuccinimide (PEG-NHS) second precursor. The at least one of the PEG-NH first precursor or the PEG-NHS second precursor combined with a hydrocarbon solvent may be one of a 4-armed or an 8-armed compound.

In exemplary embodiments, the active-containing powder combined with the hydrocarbon solvent is a protein powder. The protein powder combined with the hydrocarbon solvent may contain an antibody, antigen binding fragment thereof, a fusion protein, a recombinant protein, or a fragment or truncated version thereof. In other embodiments, the protein powder combined with the hydrocarbon solvent contains vascular endothelial growth factor-Trap (VEGF-Trap) protein. The VEGF-Trap protein combined with the hydrocarbon solvent may be a truncated form of VEGF-Trap protein. In yet other embodiments, the protein powder combined with the hydrocarbon solvent may be micronized by spray-drying, electrospray drying, reversible precipitation, spray freezing, microtemplating, or a combination thereof.

In exemplary embodiments, the step of agitating the combined first and second solutions may include homogenization, vortexing, sonication, cavitation, agitation, or a combination thereof. The isolated microparticles may be sustained release microparticles. The first non-aqueous solution formed may include 1.0% to 30% w/v of a spray dried-protein suspended in the hydrocarbon solvent and 5.0% to 35% w/v of the one or more of the cross linkable polymer precursors. The second solution to which the first non-aqueous solution is added may contain 0.1% to 5.0% w/v of the fluorosurfactant.

In exemplary embodiments, the method may further include the step of suspending the microparticles in a pharmaceutically acceptable excipient. The microparticles may be suspended in pH buffered saline.

In another embodiment, the present disclosure relates to a method for producing polymeric or polymer-coated microspheres including the steps of combining a dispersed phase including 1.0% to 30.0% w/w of total solid spray dried-protein suspended in a first non-aqueous hydrocarbon solution, wherein the first non-aqueous hydrocarbon solution comprises 5.0% to 35% w/v PEG-NH and 1.0% to 15% w/v PEG-NH, into a continuous phase to form emulsion droplets of the dispersed phase. The continuous phase may include a second non-aqueous fluorocarbon solution comprising 0.1% to 5.0% w/v fluorosurfactant. The method further includes the step of hardening the emulsion droplets by removing the hydrocarbon liquids to form hardened polymer or polymer-coated microspheres.

In some exemplary embodiments, a method of producing hydrogel microparticles according to the present disclosure comprises (a) combining at least one crosslinkable polymer, at least one crosslinking modulator, and a powder including at least one protein with a hydrocarbon solvent to form a dispersed phase suspension; (b) adding said dispersed phase suspension to a continuous phase solution, wherein said solution comprises a fluorocarbon liquid and a fluorosurfactant, to form a combined dispersed phase suspension and continuous phase solution; (c) applying blending forces to said combined dispersed phase suspension and continuous phase solution to form a non-aqueous emulsion having multiple hydrocarbon droplets including said at least one crosslinkable polymer and said powder further including at least one protein in the fluorocarbon liquid; and (d) removing the hydrocarbon solvent and the fluorocarbon liquid from said non-aqueous emulsion to form isolated hydrogel microparticles, wherein said hydrogel microparticles include said at least one protein encapsulated within a matrix of said crosslinked polymer.

In one aspect, the at least one crosslinking modulator is a non-functionalized linear PEG polymer. In another aspect, a concentration of the at least one crosslinking modulator in the dispersed phase is between about 5.0% and about 35% w/v.

In one aspect, the fluorocarbon liquid is a high viscosity fluorocarbon. In another aspect, the continuous phase solution comprises a perfluoro C5-C18 compound. In yet another aspect, the continuous phase solution comprises Fluorinert™ FC-70 or perfluorotripentylamine.

In one aspect, the hydrocarbon solvent is selected from a group consisting of dichloromethane, chloroform, toluene, ethyl acetate, tetrahydrofuran, and a combination thereof. In another aspect, the continuous phase solution comprises perfluoropolyether-b-polyethylene glycol-b-perfluoropolyether.

In one aspect, the at least one crosslinkable polymer includes a core selected from a group consisting of polyethylene glycol, polyethylene oxide, polyethylene oxide-co-polypropylene oxide, co-polyethylene oxide block or random copolymers, polyvinyl alcohol, poly(vinyl pyrrolidinone), poly(amino acids), dextran, and any combination thereof.

In one aspect, the at least one crosslinkable polymer comprises a first crosslinkable polymer including at least one nucleophilic functional group, and a second crosslinkable polymer including at least one electrophilic functional group. In a specific aspect, the molar ratio of the at least one nucleophilic functional group to the at least one electrophilic functional group is between about 1:1 and about 1:2. In another specific aspect, the at least one crosslinkable polymer comprises a PEG-NH first precursor, and a PEG-NHS second precursor. In a further specific aspect, the PEG-NH first precursor or the PEG-NHS second precursor is a 4-armed or an 8-armed compound.

In one aspect, the at least one protein is an antibody, an antigen-binding fragment thereof, a fusion protein, a recombinant protein, or a fragment or truncated version thereof. In a specific aspect, the at least one protein is a VEGF-Trap protein. In a further specific aspect, the VEGF-Trap protein is a truncated form of VEGF-Trap protein.

In one aspect, the at least one protein is selected from a group consisting of aflibercept, rilonacept, alirocumab, dupilumab, sarilumab, cemiplimab, anti-Ebola antibodies, and anti-severe acute respiratory syndrome coronavirus 2 (anti-SARS-CoV-2) antibodies.

In one aspect, the isolated hydrogel microparticles have a diameter between about 1 m and about 200 μm. In another aspect, the powder is micronized by spray-drying, electrospray drying, reversible precipitation, spray freezing, microtemplating, or a combination thereof. In a further aspect, the blending forces comprise homogenization, vortexing, sonication, cavitation, agitation, or a combination thereof.

In one aspect, the hydrogel microparticles are sustained release microparticles.

In one aspect, a concentration of the powder in the dispersed phase suspension is between about 1.0% and about 30% w/v. In another aspect, a concentration of the at least one crosslinkable polymer in the dispersed phase suspension is between about 5.0% and about 35% w/v. In yet another aspect, a concentration of the fluorosurfactant in the continuous phase solution is between about 0.1% and about 5.0% w/v.

In one aspect, the method further comprises suspending the isolated hydrogel microparticles in a pharmaceutically acceptable formulation. In another aspect, the formulation comprises pH buffered saline, an aqueous solution, or a non-aqueous solution.

In one aspect, the powder further comprises at least one excipient.

This disclosure also provides a hydrogel microparticle. In some exemplary embodiments, the hydrogel microparticle is produced by any of the aforementioned methods.

These, and other, aspects of the present invention will be better appreciated and understood when considered in conjunction with the following description and accompanying drawings. The following description, while indicating various embodiments and numerous specific details thereof, is given by way of illustration and not of limitation. Many substitutions, modifications, additions, or rearrangements may be made within the scope of the invention.

BRIEF DESCRIPTION OF THE DRAWINGS

A more complete understanding of the presently disclosed concepts and illustrative embodiments may be acquired by referring to the following description, taken in conjunction with the figures of the accompanying drawings.

FIG. 3 illustrates the process of preparing drug microparticles having spray-dried protein (SDP) encapsulated in a crosslinked PEG microgel according to an exemplary embodiment.

FIG. 4A shows a bright field microscopy image of VEGF-Trap encapsulating crosslinked PEG microgels according to an exemplary embodiment suspended in Fluorinert™ FC-70.

FIG. 4B shows a fluorescence microscopy image of VEGF-Trap encapsulating crosslinked PEG microgels according to an exemplary embodiment suspended in Fluorinert™ FC-70.

FIG. 5A shows a bright field microscopy image of VEGF-Trap encapsulating crosslinked PEG microgels according to an exemplary embodiment suspended in Fluorinert™ FC-70.

FIG. 5B shows a fluorescence microscopy image of VEGF-Trap encapsulating crosslinked PEG microgels according to an exemplary embodiment suspended in Fluorinert™ FC-70.

FIG. 6A shows a bright field microscopy image of VEGF-Trap encapsulating crosslinked PEG microgels according to an exemplary embodiment suspended in water.

FIG. 6B shows a fluorescence microscopy image of VEGF-Trap encapsulating crosslinked PEG microgels according to an exemplary embodiment suspended in water.

DETAILED DESCRIPTION

Figure 1A:
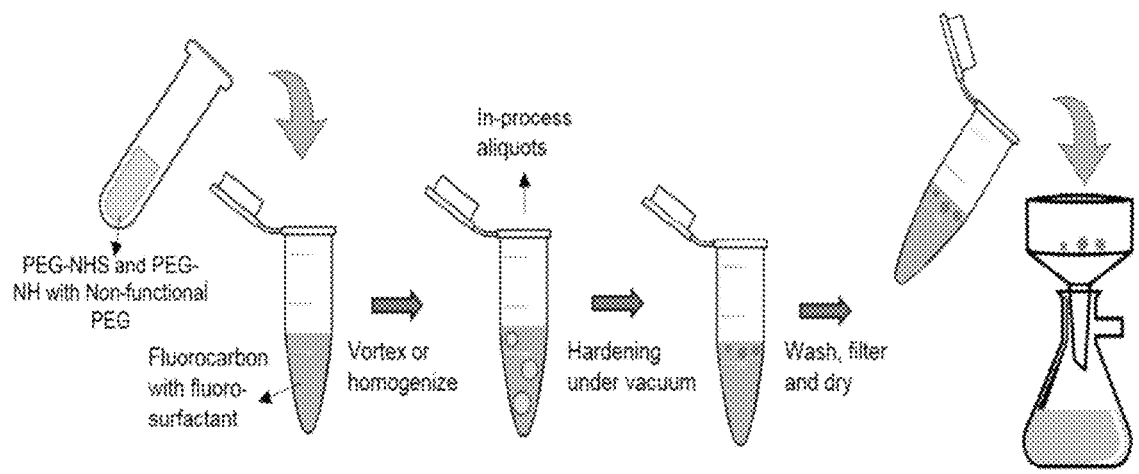
FIG. 1A illustrates a process for producing blank cross-linked PEG microgels via hydrocarbon in fluorocarbon (H/F) based (non-aqueous) bulk emulsion according to an exemplary embodiment.

It should be appreciated that this disclosure is not limited to the materials, compositions and methods described herein or the experimental conditions described, as such materials, compositions, methods and/or conditions may vary. It should also be understood that the terminology used herein is for the purpose of describing certain embodiments only and is not intended to be limiting.

Unless defined otherwise, all technical and scientific terms used herein have the same meaning as commonly understood by one of ordinary skill in the art to which this disclosure pertains. Any compositions, methods, and materials similar or equivalent to those described herein can be used in the practice or testing of the various aspects of the embodiments described herein.

The use of the terms "a," "an," "the," and similar referents in the context of describing the various aspects of the embodiments presented herein (especially in the context of the claims) are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein.

The term "about" is intended to describe values either above or below the stated value in a range of approximately +/−10%; in other exemplary embodiments the values may range in value either above or below the stated value in a range of approximately +/−5%; in other exemplary embodiments the values may range in value either above or below the stated value in a range of approximately +/−2%; in other exemplary embodiments the values may range in value either above or below the stated value in a range of approximately +/−1%. The preceding ranges are intended to be made clear by context, and no further limitation is implied.

All methods described herein can be performed in any suitable order unless otherwise indicated herein or otherwise clearly contradicted by context. The use of any and all examples or exemplary language (e.g., "such as") provided herein is intended merely to better illuminate the various aspects of the embodiments described herein and does not pose a limitation on the scope of the disclosure unless otherwise claimed. No language in the specification should be construed as indicating any non-claimed element as essential to the practice of the various aspects of the embodiments described herein.

The term "protein" refers to a molecule including two or more amino acid residues joined to each other by a peptide bond. Protein includes polypeptides and peptides and may also include modifications such as glycosylation, lipid attachment, sulfation, gamma-carboxylation of glutamic acid residues, alkylation, hydroxylation and ADP-ribosylation. Proteins can be of scientific or commercial interest, including protein-based drugs, and proteins include, among other things, enzymes, ligands, receptors, antibodies and chimeric or fusion proteins. Proteins may be produced by various types of recombinant cells using well-known cell culture methods, and may generally be introduced into the cell by genetic engineering techniques (for example, a sequence encoding a chimeric protein, or a codon-optimized sequence, an intronless sequence, etc.) where it may reside as an episome or be integrated into the genome of the cell.

The term "antibody" refers to an immunoglobulin molecule consisting of four polypeptide chains, two heavy (H) chains and two light (L) chains inter-connected by disulfide bonds. Each heavy chain has a heavy chain variable region (HCVR or VH) and a heavy chain constant region. The heavy chain constant region contains three domains, CH1, CH2 and CH3. Each light chain has a light chain variable region and a light chain constant region. The light chain constant region consists of one domain (CL). The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The term "antibody" includes reference to both glycosylated and non-glycosylated immunoglobulins of any isotype or subclass. The term "antibody" includes antibody molecules prepared, expressed, created, or isolated by recombinant means, such as antibodies isolated from a host cell transfected to express the antibody. The term antibody also includes bispecific antibody, which includes a heterotetrameric immunoglobulin that can bind to more than one different epitope. Bispecific antibodies are generally described in U.S. Pat. No. 8,586,713, which is incorporated by reference into this application.

The term "Fc fusion proteins" include part or all of two or more proteins, one of which is an Fc portion of an immunoglobulin molecule, which are not otherwise found together in nature. Preparation of fusion proteins including certain heterologous polypeptides fused to various portions of antibody-derived polypeptides (including the Fc domain) has been described, e.g., by Ashkenazi et al., Proc. Natl. Acad. Sci. USA 88: 10535, 1991; Byrn et al., Nature 344:677, 1990; and Hollenbaugh et al., "Construction of Immunoglobulin Fusion Proteins", in Current Protocols in Immunology, Suppl. 4, pages 10.19.1-10.19.11, 1992. "Receptor Fc fusion proteins" include one or more extracellular domain(s) of a receptor coupled to an Fc moiety, which in some embodiments include a hinge region followed by a CH2 and CH3 domain of an immunoglobulin. In some embodiments, the Fc-fusion protein includes two or more distinct receptor chains that bind to a one or more ligand(s). For example, an Fc-fusion protein may be a trap, such as for example an interleukin-1 trap (IL-1 trap) or VEGF-Trap. In some exemplary embodiments, an Fc-fusion protein used in the present invention may be a VEGF-Trap, such as aflibercept.

The term "micronized protein particle" or "protein particle" refers to a particle containing multiple molecules of protein with low, very low, or close to zero amounts of water (for example, <3% water by weight). As used herein, a micronized protein particle is generally spherical in shape and has an equivalent circular diameter (ECD) ranging from about 2 microns to about 35 microns. A micronized protein particle is not limited to any particular protein entity and is suited to the preparation and delivery of a therapeutic protein. Common therapeutic proteins include, inter alia, antigen-binding proteins, such as, for example, soluble receptor fragments, antibodies (including immunoglobulin Gs (IgGs)) and derivatives or fragments of antibodies, other Fc containing proteins, including Fc fusion proteins, and receptor-Fc fusion proteins, including the trap-type proteins (Huang, C., Curr. Opin. Biotechnol. 20: 692-99 (2009)) such as, for example, VEGF-Trap.

The term "hydrogel microparticles" (microgels) refers to microstructures comprising hydrophilic polymeric networks. The network of polymers is connected by crosslinks, which may have a covalent, ionic, affinity, or physical basis. Microgels have emerged as a potential delivery vehicle for controlled-release of therapeutic proteins. Compared to bulk hydrogels that require surgery to implant, soft, deformable microgels can be delivered to a patient with a needle or catheter, which is less invasive and can lead to better therapeutic outcomes. Using the fabrication processes described herein, micronized protein particles (that is, a micronized form of a protein powder, for example, spray-dried VEGF-Trap powder) may be suspended in a hydrocarbon solution containing crosslinkable polymers. Crosslinkable polymers that undergo a chemical reaction for crosslinking may also be referred to as polymer precursors.

After adding cross-linking agent, the suspension (also referred to herein as a first solution or dispersed phase suspension) may be immediately added into a fluorocarbon continuous phase containing a fluorosurfactant. The hydrocarbon phase quickly disperses through an emulsification method. As the fluorocarbon continuous phase confines the crosslinkable polymers and spray-dried protein powder inside the hydrocarbon droplets, the polymers in the emulsion droplets are crosslinked and then hardened into individual microgels.

Production of Hydrogel Microparticles Using Hydrocarbon-Fluorocarbon Emulsions

Oil and aqueous-based emulsion system are frequently used for polymeric microparticle or nanoparticle synthesis, where hydrophobic polymer materials are dissolved in the organic phase and dispersed in an aqueous continuous phase. However, for water-soluble polymers, for example PEG or carboxymethyl cellulose (CMC), and polymers that readily hydrolyze in the presence of water, for example polyanhydrides, aliphatic polyesters with short mid-blocks like polylactic acid, and certain poly (amino acids) like poly (glutamic acid), conventional aqueous-based emulsion systems are not ideal. In addition to the undesirable effect of water-soluble polymer dissolving in the aqueous continuous phase, functionalized crosslinking polymer such as PEG-NHS may react with water, causing the reaction kinetics of crosslinking to become very unfavorable for the formation of microgels.

Additionally, pharmaceutical formulations produced using aqueous emulsion systems may leak drug, for example protein drug, from emulsion droplets into the aqueous continuous phase during production. This leakage of drug from the emulsion droplets results in low encapsulation efficacy. Water-soluble drugs such as protein drugs may dissolve in the aqueous continuous phase, preventing the gradual sustained release of drug from microgels.

Systems and methods for formulating pharmaceutical compositions using anhydrous, or non-aqueous, emulsion systems are provided. The disclosed anhydrous emulsion methods overcome the problems with existing aqueous emulsion systems described above.

The non-aqueous based emulsion methods described herein encapsulate drug molecules, including but not limited to hydrophilic drugs such as proteins, with increased encapsulation efficacy relative to aqueous emulsion systems, increased retention of original protein particulate structure, or a combination thereof. The disclosed anhydrous emulsion systems and methods can produce encapsulated drug formulations by bulk methods (for example, agitation, homogenization, or sonication) and other conventional methods. The systems and methods disclosed herein can also be applied to a wide range of polymer materials, solid-state payloads, and emulsification methods.

Solid-in-Hydrocarbon-in-Fluorocarbon (S/H/F) Emulsions

An exemplary non-aqueous S/H/F emulsion method includes the steps of combining dry protein powder, one or more biodegradable and/or bioerodible cross-linkable polymers or polymer precursors, and one or more cross-linking modulators into a hydrocarbon solvent to form a non-aqueous first solution or dispersed phase suspension, and adding the first solution or dispersed phase suspension to a second solution or continuous phase solution containing a fluorocarbon liquid and a fluorosurfactant. The combination of the first solution or dispersed phase suspension and second solution or continuous phase solution is done in a manner to form a non-aqueous emulsion containing multiple emulsion hydrocarbon droplets in the fluorocarbon liquid, for example by applying blending forces such as agitation, sonication, cavitation, homogenization, or vortexing.

The method of the present invention further includes removing the hydrocarbon solvent and removing the fluorocarbon liquid to isolate hydrogel microparticles having one or more cores of micronized protein and a cortex of cross-linked biodegradable polymer.

In some exemplary embodiments, the emulsion is stirred, and the hydrocarbon and fluorocarbon liquids are evaporated at ambient conditions or under vacuum. In some exemplary embodiments, hydrofluoroether (HFE) can be added to the fluorocarbon to help extract the hydrocarbon from the dispersed phase into the fluorocarbon continuous phase. The resulting microparticles can optionally be washed to remove hydrocarbon solvent, fluorocarbon liquid, fluorosurfactant, or a combination thereof. The emulsion can be formed using bulk emulsion techniques. Removing the hydrocarbon and fluorocarbon liquids hardens the microparticles, which can then be harvested.

In some exemplary embodiments, the microparticles may be harvested by filtration. The sustained release microparticles produced by the present non-aqueous emulsion methods contain protein encapsulated within a matrix of a cross-linked biodegradable and/or bioerodible polymer. In some exemplary embodiments, the microparticles have a single core-shell structure. In other exemplary embodiments, the microparticles have multiple cores dispersed within the polymer.

In still other exemplary embodiments, the population of microparticles includes both microparticles having a single core-structure encapsulated by a polymer cortex, and microparticles having multi-core structures in the polymer cortex. The fluorocarbon liquid may be a high viscosity fluorocarbon such as a perfluoro C5-C18 compound, including, but not limited to, a mixture of perfluoro(dibutylmethylamine) and perfluorotributylamine, sold under the trademark Fluorinert™ FC-40, or perfluorotripentylamine, and the hydrocarbon solution may include a hydrocarbon solvent selected from ethyl acetate, chloroform, toluene, tetrahydrofuran, and dichloromethane, or combinations thereof. In some exemplary embodiments, the fluorosurfactant is perfluoropolyether-b-polyethylene glycol-b-perfluoropolyether, sold under the trademark Pico-Surf™ 1.

In some exemplary embodiments, a concentration of a fluorosurfactant in the continuous phase solution may be between about 0.1% and about 10% w/v, between about 0.1% and about 5% w/v, between about 1% and about 10% w/v, between about 1% and about 5% w/v, about 0.1% w/v, about 0.2% w/v, about 0.3% w/v, about 0.4% w/v, about 0.5% w/v, about 0.6% w/v, about 0.7% w/v, about 0.8% w/v, about 0.9% w/v, about 1% w/v, about 1.5% w/v, about 2% w/v, about 2.5% w/v, about 3% w/v, about 3.5% w/v, about 4% w/v, about 4.5% w/v, about 5% w/v, or about 10% w/v.

Crosslinkable Polymers and Polymer Precursors

Precursors suitable for producing the crosslinked polymer cortex of the hydrogel microparticles of the present invention are typically multifunctional, meaning that they include two or more electrophilic or nucleophilic functional groups, such that a nucleophilic functional group on one precursor may react with an electrophilic functional group on another precursor to form a covalent bond. Precursors may include more than two functional groups, so that, as a result of electrophilic-nucleophilic reactions, the precursors combine to form crosslinked polymeric products. Such reactions are referred to as "crosslinking reactions." In some exemplary embodiments, more than one precursor may be employed, where a first precursor is a polymer precursor (containing, for example, electrophilic groups), and a second precursor is a low molecular weight compound (containing, for example, nucleophilic groups). It should be understood that one, two, three, four or more different precursors may be employed depending on the desired characteristics of the cortex, provided that at least one of the precursors is polymeric.

In some exemplary embodiments, each precursor includes only nucleophilic or only electrophilic functional groups, so long as both nucleophilic and electrophilic precursors are used in the crosslinking reaction. Thus, for example, if a crosslinker (having a relatively low molecular weight) has nucleophilic functional groups such as amines, a functional polymer (having a relatively high molecular weight) may have electrophilic functional groups such as N-hydroxysuccinimides. On the other hand, if a crosslinker has electrophilic functional groups such as sulfosuccinimides, then a functional polymer may have nucleophilic functional groups such as amines. Thus, functional polymers such as proteins, poly(allyl amine), or amine-terminated di- or multifunctional poly(ethylene glycol) ("PEG") can be used.

In some exemplary embodiments, the number of nucleophilic groups in a first precursor can be about 2-30, about 2-25, about 2-20, about 2-15, about 2-10, about 5-30, about 5-20, about 5-15, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, or about 30.

In some exemplary embodiments, the number of electrophilic groups in a second precursor can be about 2-30, about 2-25, about 2-20, about 2-15, about 2-10, about 5-30, about 5-20, about 5-15, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, or about 30.

Crosslinkable polymers or polymer precursors may have biologically inert and water-soluble cores. In the case of a branched polymer, a core refers to a contiguous portion of a molecule joined to arms that extend from the core, with the terminus of each arm having a functional group. When the core is a polymeric region that is water soluble, suitable polymers that may be used include polyethers, for example polyalkylene oxides such as polyethylene glycol ("PEG"); polyethylene oxide ("PEO"); polyethylene oxide-co-polypropylene oxide ("PPO"); co-polyethylene oxide block or random copolymers, and polyvinyl alcohol ("PVA"); poly (vinyl pyrrolidinone) ("PVP"); poly(amino acids); dextran; and the like. When the core is small molecular in nature, any of a variety of hydrophilic functionalities can be used to make the precursor water soluble. For example, functional groups like hydroxyl, amine, sulfonate, and carboxylate, which are water soluble, maybe used to make the precursor water soluble. In addition, N-hydroxysuccinimide ("NHS") ester of subaric acid is insoluble in water, but by adding a sulfonate group to the succinimide ring, the NHS ester of subaric acid may be made water soluble, without affecting its reactivity towards amine groups.

To provide a biocompatible crosslinked polymer that is biodegradable or absorbable, one or more precursors having biodegradable linkages present in between the functional groups may be used. The biodegradable linkage optionally also may serve as the water-soluble core of one or more of the precursors. In the alternative, or in addition, the functional groups of the precursors may be chosen such that the product of the reaction between them results in a biodegradable linkage. For each approach, biodegradable linkages may be chosen such that the resulting biodegradable, biocompatible crosslinked polymer will degrade or be absorbed in a desired period of time. Biodegradable linkages may be selected that degrade under physiological conditions into non-toxic products.

The biodegradable linkage may be chemically or enzymatically hydrolyzable or absorbable. Examples of chemically hydrolyzable biodegradable linkages include polymers, copolymers, and oligomers of glycolide, dl-lactide, 1-lactide, caprolactone, dioxanone, and trimethylene carbonate. Examples of enzymatically hydrolyzable biodegradable linkages include peptidic linkages cleavable by metalloproteinases and collagenases. Additional examples of biodegradable linkages include polymers and copolymers of poly(hydroxy acid)s, poly(orthocarbonate)s, poly(anhydride)s, poly(lactone)s, poly(aminoacid)s, poly(carbonate)s, and poly(phosphonate)s.

Certain functional groups, such as alcohols or carboxylic acids, do not normally react with other functional groups, such as amines, under physiological conditions (for example, pH 7.2-11.0, 37° C.). However, such functional groups can be made more reactive by using an activating group such as N-hydroxysuccinimide. Several methods for activating such functional groups are known in the art. Suitable activating groups include carbonyldiimidazole, sulfonyl chloride, aryl halides, sulfosuccinimidyl esters, N-hydroxysuccinimidyl ester, succinimidyl ester, epoxide, aldehyde, maleimides, imidoesters and the like. N-hydroxysuccinimide esters or N-hydroxysulfosuccinimide groups are suitable groups for crosslinking of proteins or amine functionalized polymers such as aminoterminated polyethylene glycol ("APEG").

Suitable biocompatible crosslinked polymers from water soluble precursors having electrophilic and nucleophilic groups capable of reacting and crosslinking in situ, and methods for their preparation and use, are disclosed, for example, in U.S. Application No. Pat. No. 8,535,70, which is incorporated herein by reference. In some exemplary embodiments, the bioerodible, crosslinkable polymer precursor is PEG-NHS.

In some exemplary embodiments, instead of polymer precursors that may crosslink using a chemical reaction, crosslinkable polymers may be used that crosslink using a physical interaction. As used herein, the term "crosslinkable polymer" encompasses polymer precursors and physically-interacting crosslinkable polymers, any of which may be suitable for the method of the present invention.

The duration of release and the release profile of the therapeutic agent depends on factors such as the crosslink density in the polymer cortex, diffusion of the protein out of the matrix, and dissolution of the matrix itself. The properties of the polymer cortex may be adjusted through several factors, including branching of the crosslinkable polymer (4-arm or 8-arm), length of the arms of the crosslinkable polymer, and the molar ratio (MR) of —NHS group to —NH groups.

The molar ratio of the nucleophilic group to the electrophilic group can determine the crosslink density. A molar ratio of 1 results in the highest crosslink density. A molar ratio of greater or less than 1 can lead to lower crosslink density than a molar ratio of one. The crosslink density increases as the molar ratio increases until it reaches the value of 1, then the crosslink density decreases as the molar ratio increases beyond the value of 1. A drug embedded in the hydrogel can be released faster when the crosslink density is lower. As a result, by adjusting the molar ratio of the nucleophilic group to the electrophilic group, the release kinetics of a drug may be adjusted.

The molar ratio may effectively modulate both the crosslink density (the number of covalent crosslinks forming the network) and the network pore size within the hydrogel matrix. By decreasing the crosslink density, the effective pore size of the matrix can be increased, resulting in faster diffusion of drug through the matrix. Additionally, decreasing crosslink density can increase domains in the hydrogel where the local concentration of crosslinking polymer surrounding a protein particle is insufficient to retain protein in the solid state upon hydration, leading to an increase in burst release as well as the rate of diffusion on a mass basis. Thus as molar ratio increases, both burst release and release kinetics in the diffusion controlled regime may increase.

Additionally, Chen et al. (U.S. Pat. Appln. Pub. No. US2020/0038328A1, which is incorporated herein by reference) observed an increase in the slope of the release profile in the dissolution-controlled regime with increasing molar ratio. This can be explained by the reduction in the extent of cross-linking with increasing molar ratio, as there is a greater mismatch between the number of nucleophilic groups and electrophilic groups available to react and cross-link. The growth rate is determined by the rate of hydrolysis of the crosslinks, leading to an increase in hydrogel swelling and a concomitant decrease in local concentrations of crosslinking polymer that result in additional dissolution of protein particles. Swelling of the hydrogel is also correlated with hydrogel porosity, which is increased as protein dissolution occurs. As molar ratio increases and protein dissolution upon hydration increases, so will the effective porosity of the hydrogel, leading to more swelling, a faster hydrolysis, and faster growth rate in the dissolution-controlled regime. Furthermore, the inflection point identifying the transition between diffusion and dissolution-controlled regimes will be inversely correlated with molar ratio. As effective rates of diffusion increase with increasing molar ratio, the time it takes for diffusion to increase to the extent that it is no longer the rate-limiting step decreases, and thereby shifts the inflection point to earlier time points. Considered comprehensively, varying the molar ratio alone can permit the release profile to be tuned from near linear to sigmoidal depending on the desired result.

In some exemplary embodiments, the molar ratio of the nucleophilic group to the electrophilic group is greater than 1. In other exemplary embodiments, the molar ratio of the nucleophilic group to the electrophilic group is less than 1. In other exemplary embodiments, the molar ratio of the nucleophilic group to the electrophilic group can be in the range of about 0.1 to 3.0, for example about 0.1 to 0.9, about 0.1 to 0.8, about 0.1 to 0.7, about 0.1 to 0.6, about 0.2 to 0.9, about 0.2 to 3.0, about 0.2 to 2.8, about 0.2 to 2.5, about 0.5 to 2.5, about 0.5 to 2.0, about 0.8 to 2.5, about 0.8 to 2.0, about 1.1 to 2.0, about 1.1 to 2.5, about 1.1 to 3.0, about 1.5 to 3.0, about 1.5 to 2.5, about 1.5 to 2.0, or about 1.3 to 1.8. In some exemplary embodiments, the molar ratio of the nucleophilic group to the electrophilic group can be about 0.1, about 0.2, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, or about 3.0.

Related to the molar ratio, the number of nucleophilic groups in a first precursor and/or the number of electrophilic groups in a second precursor can also determine the crosslink density. Generally, at a given molar ratio, the higher the number of nucleophilic or electrophilic groups, the higher the crosslink density. In some embodiments, the method comprises selecting 8-arm PEG NH and 8-arm PEG NHS reagents for a release period of 60 days or longer. In some embodiments, the method comprises selecting 4-arm PEG NH and 4-arm PEG NHS reagents for a release period of less than 60 days.

Another parameter that can be used to tune the release kinetics of a hydrogel microparticle is the molecular weight of a first and/or second crosslinkable polymer. At a given molar ratio, the lower the molecular weight of a crosslinkable polymer, the smaller the network pore size. The molecular weights of a first and second crosslinkable polymer have a non-continuous or discrete effect on release profile. As used herein, the term "non-continuous" or "discrete" means that one cannot interpolate between levels. For example, a combination of first and second crosslinkable polymers (for example, PEG reagents) with predetermined molecular weights can define a range of release periods possible. Other factors such as molar ratio can be used to fine tune the release profile or release period.

Another parameter that one can use to tune the release kinetics is a weight ratio of the drug and excipients to the hydrogel. The weight ratio of the drug and excipients to the hydrogel is also referred to herein as "solid loading." This refers to the weight ratio of the drug and excipients to the total weight of the drug, excipients, and polymer comprising the drug-loaded hydrogel. Increasing the solid loading can change the shape of the release profile, primarily due to faster release during the initial diffusion phase before the inflection point. There is also likely an inverse correlation between the onset of the dissolution phase (the inflection point) and the solid loading. Without wishing to be bound by theory, with increased solid loading, faster release during the initial diffusion phase is expected because there will be a larger quantity of drug in microenvironments of relatively low crosslinkable polymer concentration where drug solubility is less limited. Drug in such regions may be dissolved upon initial hydration of the matrix, increasing the rate of concentration-dependent diffusion. Additionally, for drug in the form of protein particles, the increase in protein particles dissolved upon initial hydration will create voids within the matrix and lead to an increase in matrix porosity. A more porous matrix will also increase the effective rate of diffusion through the bulk matrix and released as it reaches the surface. Without wishing to be bound by theory, the inverse correlation between inflection point and solid loading can also be hypothetically explained by the increase in rate of diffusion observed with increased solid loading. The inflection point signifies the transition between a diffusion-controlled regime and a dissolution-controlled regime. As solid loading increases, the diffusion rate starts higher and increases more rapidly, leading to a shorter duration before diffusion is no longer rate limiting. In the diffusion-controlled regime, diffusion of dissolved drug through the matrix is the rate-limiting step for drug release. As more protein particles dissolve, voids within the matrix are created and the porosity of the matrix increases, leading to increased rates of diffusion. In the dissolution-controlled regime, diffusion through the matrix is no longer the rate-limiting step. This point is reached more rapidly as solid loading increases.

In some exemplary embodiments, a concentration of crosslinkable polymers or polymer precursors in a dispersed phase suspension may be between about 1% and about 50% w/v, between about 1% and about 35% w/v, between about 1% and about 20% w/v, between about 5% and about 50% w/v, between about 5% and about 35% w/v, between about 5% and about 20% w/v, about 1% w/v, about 2% w/v, about 3% w/v, about 4% w/v, about 5% w/v, about 6% w/v, about 7% w/v, about 8% w/v, about 9% w/v, about 10% w/v, about 15% w/v, about 20% w/v, about 25% w/v, about 30% w/v, about 35% w/v, about 40% w/v, about 45% w/v, or about 50% w/v.

In some exemplary embodiments, the present disclosure provides a method for producing polymer-coated microspheres by combining (1) a dispersed phase having 1.0% to 30.0% w/v spray-dried protein suspended in a hydrocarbon solution, wherein the hydrocarbon solution comprises 5.0% to 35% w/v of one or more crosslinkable polymers in a hydrocarbon solvent, with (2) a continuous phase to form emulsion droplets of the dispersed phase, wherein the continuous phase comprises a fluorocarbon solution containing 0.1% to 5.0% w/v fluorosurfactant. The method further includes hardening the emulsion droplets by removing the hydrocarbon solution to form hardened cross-linked polymer-coated microspheres.

In some exemplary embodiments, the fluorocarbon solution may be a high viscosity fluorocarbon such as a perfluoro C5-C18 compound, including, but not limited to, FC-40 or FC-70, and the hydrocarbon solution may be selected from a group including ethyl acetate, chloroform, toluene, tetrahydrofuran, dichloromethane, or combinations thereof. In some exemplary embodiments, the fluorosurfactant may be perfluoropolyether-b-polyethylene glycol-b-perfluoropolyether, sold under the trademark Pico-Surf™ 1. The method may also include stirring the emulsion while under vacuum to remove the hydrocarbon, adding hydrofluoroether (HFE) to accelerate hardening of microspheres, and/or filtering to remove fluorocarbon solutions.

In other exemplary embodiments, spray-dried proteins may be encapsulated in cross-linked polyethylene glycol microgels. Crosslinking of PEG may be achieved through mixing a PEG precursor containing nucleophilic groups, such as for example, PEG-NH, with a PEG precursor containing electrophilic groups, such as for example, PEG-NHS. In some exemplary embodiments, addition of non-functionalized PEG to the reaction mixture may be used to modulate the cross-linking reaction speed, as the non-functionalized PEG maintains the hydrocarbon phase viscosity while reducing the functionalized PEG precursor concentration. Thus, varying the ratio of functionalized PEG precursor to cross-linking modulator (pure non-functionalized PEG) may be used to achieve a desired gelation time.

In some exemplary embodiments, a concentration of a cross-linking modulator in a dispersed phase suspension may be between about 1% and about 50% w/v, between about 1% and about 35% w/v, between about 1% and about 20% w/v, between about 5% and about 50% w/v, between about 5% and about 35% w/v, between about 5% and about 20% w/v, about 1% w/v, about 2% w/v, about 3% w/v, about 4% w/v, about 5% w/v, about 6% w/v, about 7% w/v, about 8% w/v, about 9% w/v, about 10% w/v, about 15% w/v, about 20% w/v, about 25% w/v, about 30% w/v, about 35% w/v, about 40% w/v, about 45% w/v, or about 50% w/v.

Still other exemplary embodiments provide methods for producing cross-linked polymer-coated microparticles by preparing a hydrocarbon solution containing dissolved cross-linkable polymer(s) and spray-dried protein powder to produce a dispersed phase. The method further includes combining the dispersed phase with a continuous phase to produce emulsion droplets of the dispersed phase in the continuous phase, wherein the continuous phase comprises a fluorocarbon liquid and 0.1% to 5.0% w/v of a fluorosurfactant, and harvesting the polymer-coated microparticles. The hydrocarbon solution may include a hydrocarbon solvent selected from a group including ethyl acetate, dichloromethane, chloroform, or a combination thereof. The fluorocarbon solution may be a high viscosity fluorocarbon. In exemplary embodiments, the fluorocarbon solution may contain FC-40 or FC-70, and the fluorosurfactant may be perfluoropolyether-b-polyethylene glycol-b-perfluoropolyether.

Hydrocarbon Solvents

In some exemplary embodiments, the hydrocarbon solvent (also referred to as hydrocarbon liquid) is selected so that polymeric materials, for example, the biodegradable or bioerodible crosslinkable polymers, are soluble in the hydrocarbon. In some embodiments, the hydrocarbon solvent is selected from a group including dichloromethane, chloroform, toluene, ethyl acetate, tetrahydrofuran, or a combination thereof. In some embodiments, the hydrocarbon solvent can contain acetonitrile, dimethylformamide, dimethylsulfoxide, acetone, ethanol, methanol, pentane, propanol, hexane, or a combination thereof.

Fluoroliquids

An exemplary fluoroliquid is a fluorocarbon liquid including, but not limited to, a mixture of completely fluorinated aliphatic compounds including perfluoro(dibutylmethylamine) and perfluorotributylamine (1,1,2,2,3,3,4,4,4-nonafluoro-N,N-bis(1,1,2,2,3,3,4,4,4-nonafluorobutyl)butan-1-amine) (average molecular weight (MW)=650 g/mol), sold under the trademark Fluorinert™ FC-40, perfluorotripentylamine (average MW=821 g/mol), sold under the trademark Fluorinert™ FC-70, or a combination thereof. In some exemplary embodiments, the fluorocarbon liquid is or comprises hydrofluoroether (HFE). An exemplary HFE includes, but is not limited to, 1-methoxyhepta fluoropropane, sold under the trademark NOVEC™ 7000 methoxy-nonafluorobutane, sold under the trademark NOVEC™ 7100, ethoxy-nonafluorobutane, sold under the trademark NOVEC™ 7200, or 2-(Trifluoromethyl)-3-ethoxydodecafluorohexane, sold under the trademark NOVEC™ 7500. In still other exemplary embodiments, the fluorocarbon liquid comprises Fluorinert™ FC-40, Fluorinert™ FC-70, Novec™ 7500, Novec™ 7100, Novec™ 7000, or combinations thereof. In certain embodiments, the second solution or continuous phase solution comprises a fluorosurfactant (FS) in addition to the fluoroliquid. An exemplary FS is perfluoropolyether-b-polyethylene glycol-b-perfluoropolyether (PFPE-PEG-PFPE) tri-block co-polymer, sold under the trademark Pico-Surf™ 1. In some exemplary embodiments, the fluorocarbon liquid or the second solution or continuous phase solution comprises Fluorinert™ FC-40 and Pico-Surf™ 1.

In some exemplary embodiments the FS is:

In some exemplary embodiments, the HFE has the following chemical structure, corresponding to 2-(Trifluoromethyl)-3-ethoxydodecafluorohexane:

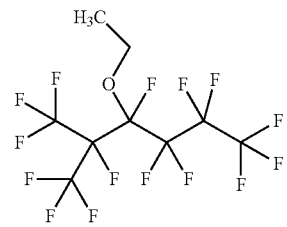 [SMILES: CCOC(F)(C(F)(F)C(F)(F)C(F)(F)F)C(F)(C(F)(F)F)C(F)(F)F]

Figure 1B:
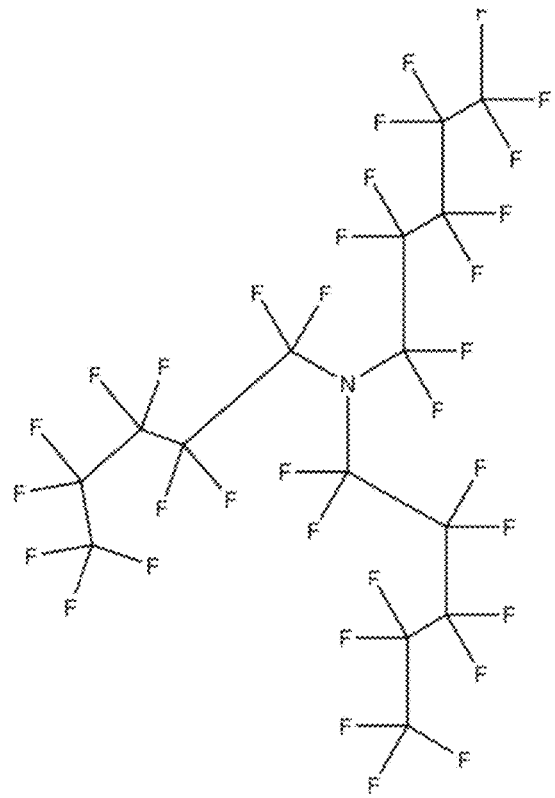
FIG. 1B shows the chemical structure for perfluorotripentylamine according to an exemplary embodiment.
Figure 1C:
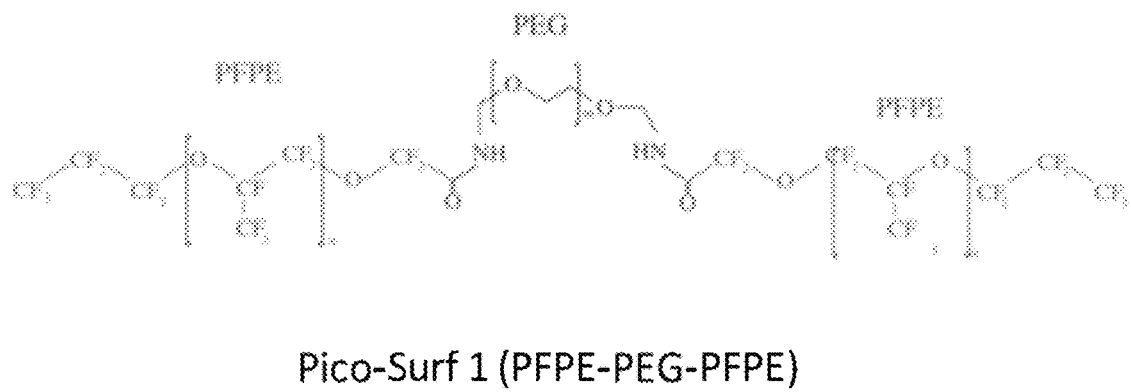
FIG. 1C shows the chemical structure for the fluorosurfactant PFPE-PEG-PFPE, sold by Sphere Fluidics under the trademark Pico-Surf™ 1, a perfluoropolyether/poly(ethylene glycol) triblock copolymer, according to an exemplary embodiment.
Figure 2:
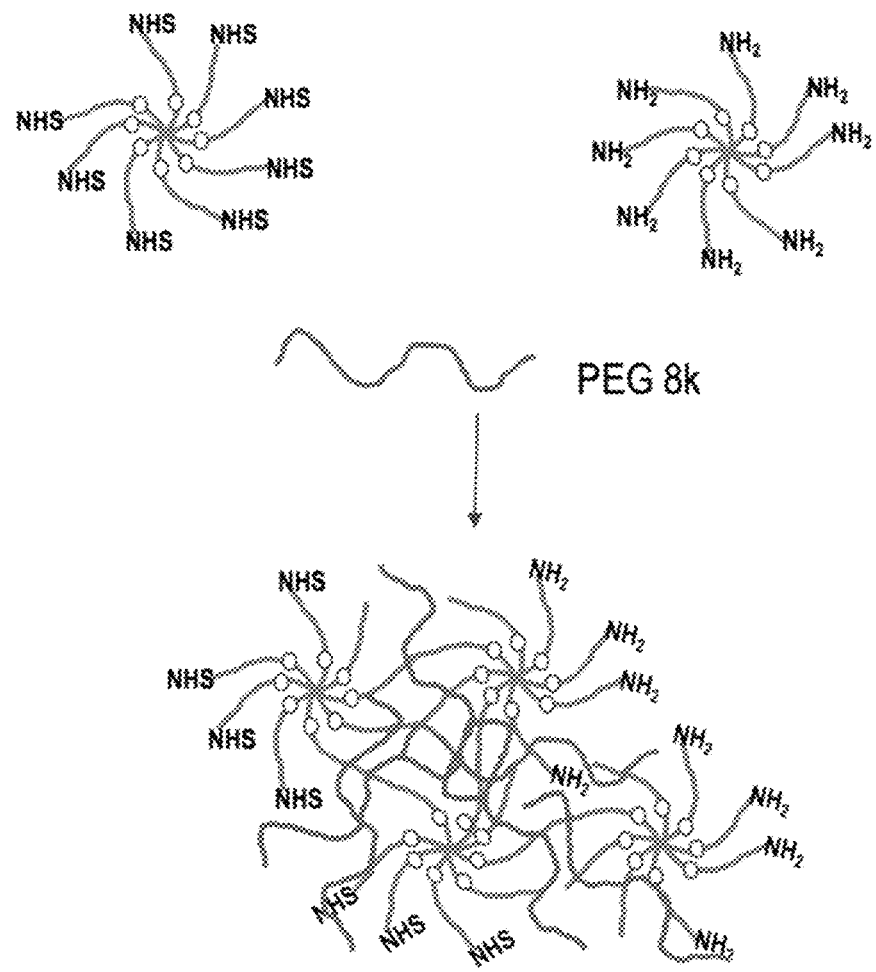
FIG. 2 illustrates a synthesis route for a blank crosslinked PEG microgel according to an exemplary embodiment.
Figure 7:
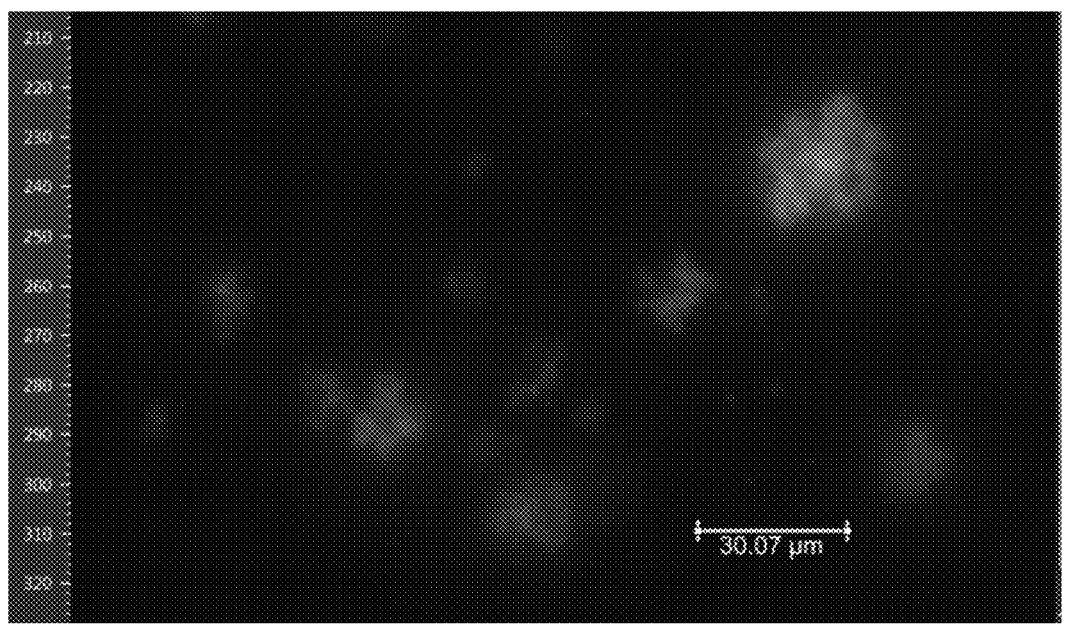
FIG. 7 shows a fluorescence microscopy image of VEGF-Trap encapsulating crosslinked PEG microgels according to an exemplary embodiment suspended in water.

In other exemplary embodiments, the fluorocarbon liquid or the second solution or continuous phase solution comprises Fluorinert™ FC-70, having a structure as illustrated in FIG. 1B.

Other HFEs suitable for use in methods in accordance with the present disclosure include the class of molecules wherein all of the hydrogen atoms reside on carbons with no fluorine substitution, and are separated from the fluorinated carbons by the ether oxygen, i.e. RfORh. HFEs have molecular structures which can be linear, branched, or cyclic, or a combination thereof (such as alkylcycloaliphatic), and are preferably free of ethylenic unsaturation, having a total of about 4 to about 20 carbon atoms. Such HFEs are known and are readily available, either as essentially pure compounds or as mixtures. Due to the lipophilicity and fluorophilicity of HFEs, they are miscible with both fluorocarbon and hydrocarbon. When added to the hydrocarbon/fluorocarbon emulsion they can act as a co-solvent to extract hydrocarbon to the fluorocarbon phase and accelerate the hardening process.

In some exemplary embodiments, the hydrocarbon solvent, the fluorocarbon, or both are removed by evaporation, optionally under vacuum, while the emulsion is stirring. In some exemplary embodiments, the microparticles are harvested by filtering, optionally filtering under vacuum.

The percentage of HFE in the fluorocarbon phase can be 0-40% v/v, depending on the lipophilicity and fluorophilicity of different HFEs. Increasing the HFE percentage increases the hydrocarbon extraction rate. However, the percentage of HFE should not be too high as the size and morphology of the microparticle may become harder to control.

Erodible or Biodegradable Polymer Cross-Linking Modulators

In order to maintain the hydrocarbon phase viscosity while reducing the functionalized crosslinkable polymer concentration, a cross-linking modulator may be added to the hydrocarbon phase. This will decrease the cross-linking

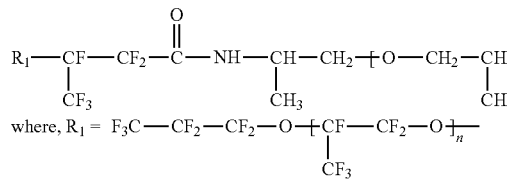

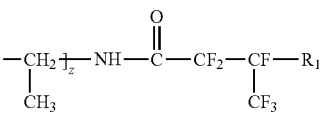

wherein: n~37, x+z~6.0, y~12.5, or wherein n=3.7, x+z~3.6, y~9.0. (See Lee, M. et al., Lab Chip., 7:14(3): 509-13(2014)).

reaction speed and prolong gelation time. In some exemplary embodiments, the cross-linking modulator is a non-functionalized erodible or biodegradable polymer.

In exemplary embodiments, the cross-linking modulator is a polymer selected from a group comprising branched or linear polyethylene glycol (PEG), polylactic acid (PLA), polyglycolic acid (PGA), polylactic-polyglycolic copolymer (PLGA), poly-D,L-lactide-co-glycolide (PLGA), PLGA-ethylene oxide fumarate, PLGA-alpha-tocopheryl succinate esterified to polyethylene glycol 1000 (PLGA-TGPS), polyanhydride poly[1,6-bis(p-carboxyphenoxy)hexane](pCPH), poly(hydroxybutyric acid-cohydroxyvaleric acid) (PHB-PVA), polyethylene glycol-poly (lactic acid) copolymer (PEG-PLA), poly-ε-caprolactone (PCL), poly-alkyl-cyanoacrylate (PAC), poly(ethyl)cyanoacrylate (PEC), polyisobutyl cyanoacrylate, poly-N-(2-hydroxypropyl)methacrylamide (poly(HPMA)), poly-β-R-hydroxy butyrate (PHB), poly-β-R-hydroxy alkanoate (PHA), poly-β-R-malic acid, phospholipid-cholesterol polymers, 2-dioleoyl-sn-glycero-3-phosphatidylcholine/polyethyleneglycol-distearoylphosphatidylethanolamine (DOPC/PEG-DSPE)/cholesterol, polysaccharides, cellulose, ethyl cellulose, methyl cellulose, alginates, dextran and dextran hydrogel polymers, amylose, inulin, pectin and guar gum, chitosan, chitin, heparin, hyaluronic acid, cyclodextrin (CD)-based polyrotaxanes and polypseudorotaxanes, polyaspartates, polyglutamates, polylucine, leucine-glutamate co-polymers, polybutylene succinate, gelatin, collagens, fibrins, fibroin, polyorthoesters, polyorthoester-polyamidine copolymer, polyorthoester-diamine copolymers, polyorthoesters incorporating latent acids, poly(ethylene glycol)/poly(butylene terephthalate) copolymer, and combinations and copolymers thereof.

As used herein, the term "polymer" refers to a macromolecule containing repeating monomers connected by covalent chemical bonds. In some exemplary embodiments, polymers may be biocompatible, biodegradable, and/or bioerodible. A biocompatible and/or biodegradable polymer can be natural or synthetic.

In some exemplary embodiments, erodible or biodegradable polymers may be part of a network of polymers connected by crosslinks. The crosslinks may have a covalent, ionic, affinity, or physical basis. Covalent crosslinking present in exemplary embodiments in accordance with the present disclosure may utilize polymers or polymer precursors with multiple reactive functional groups that are mixed and triggered to react with each other to form matrices. For making hydrogel microparticles (microgels) using H/F emulsions, the crosslinking reactions should initiate mainly after the emulsification process and proceed within the hydrocarbon emulsion droplets to form stably crosslinked and distinct microgel particles. Thus, controlling the crosslinking reaction kinetics or gelation rate helps to produce distinct, crosslinked microgel particles with desired characteristics.

Protein Drugs

Generally, any active ingredient may be incorporated into the microparticles of the present disclosure. In some exemplary embodiments, the active ingredient is a drug. In specific exemplary embodiments, the active ingredient is a protein. Such proteins can include, but are not limited to antibodies, receptors, fusion proteins, antagonists, inhibitors, enzymes (such as those used in enzyme replacement therapy), factors and co-factors, cytokines, chemokines, repressors, activators, ligands, reporter proteins, selection proteins, protein hormones, protein toxins, structural proteins, storage proteins, transport proteins, neurotransmitters and contractile proteins. Typically, the protein is micronized, for example by spray-drying, electrospray drying, reversible precipitation, spray freezing, microtemplating, or a combination thereof. In some exemplary embodiments, the protein is a VEGF-Trap protein or a truncated form thereof. Other examples of proteins that can be used in the disclosed methods are described below.

In some exemplary embodiments, the microparticle formulations produced by the disclosed anhydrous emulsion methods and system include a drug. Exemplary drugs include, but are not limited to, proteins, fusion proteins, and fragments thereof, antibodies, and antigen-binding fragments thereof. In some exemplary embodiments, the protein is a VEGF-Trap protein (for example, aflibercept, which contains the immunoglobulin (Ig) domain 2 of the VEGF receptor Flt1 fused to the Ig domain 3 of the VEGF receptor Flk1 fused to Fc of hIgG1, for example as described in U.S. Pat. Nos. 7,087,411, 7,279,159, and 8,144,840, which are herein incorporated by reference in their entirety). In some exemplary embodiments, the VEGF-Trap protein is a truncated form of VEGF-Trap as described in U.S. Pat. No. 7,396,664, which is incorporated by reference in its entirety.

Antibodies (also referred to as "immunoglobulins") are examples of proteins having multiple polypeptide chains and extensive post-translational modifications. The canonical immunoglobulin protein (for example, IgG) comprises four polypeptide chains—two light chains and two heavy chains. Each light chain is linked to one heavy chain via a cysteine disulfide bond, and the two heavy chains are bound to each other via two cysteine disulfide bonds. Immunoglobulins produced in mammalian systems are also glycosylated at various residues (for example, at asparagine residues) with various polysaccharides, and can differ from species to species, which may affect antigenicity for therapeutic antibodies. Butler and Spearman, "The choice of mammalian cell host and possibilities for glycosylation engineering", Curr. Opin. Biotech. 30:107-112 (2014).

The antibody heavy chain constant region comprises three domains: CH1, CH2 and CH3. Each light chain comprises a light chain variable region (abbreviated herein as LCVR or VL) and a light chain constant region. The light chain constant region comprises one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. Heavy chain CDRs may be abbreviated as HCDR1, HCDR2 and HCDR3; light chain CDRs may be abbreviated as LCDR1, LCDR2 and LCDR3. The term "high affinity" antibody refers to those antibodies having a binding affinity to their target of at least $10^{-9}$ M, at least $10^{-10}$ M; at least $10^{-11}$ M; or at least $10^{-12}$ M, as measured by surface plasmon resonance (for example, a surface plasmon resonance platform sold under the trademark BIACORE™) or solution-affinity enzyme-linked immunosorbent assay (ELISA).

Antibody light chains include an immunoglobulin light chain constant region sequence from any organism, and unless otherwise specified includes human kappa and lambda light chains. Light chain variable (VL) domains typically include three light chain CDRs and four framework (FR) regions, unless otherwise specified. Generally, a full-length light chain includes, from amino terminus to carboxyl terminus, a VL domain that includes FR1-CDR1-FR2-CDR2-FR3-CDR3-FR4, and a light chain constant domain. Light chains that can be used with these inventions include those, for example, that do not selectively bind either the first or second antigen selectively bound by the antigen-binding protein. Suitable light chains include those that can be identified by screening for the most commonly employed light chains in existing antibody libraries (wet libraries or in silico), where the light chains do not substantially interfere with the affinity and/or selectivity of the antigen-binding domains of the antigen-binding proteins. Suitable light chains include those that can bind one or both epitopes that are bound by the antigen-binding regions of the antigen-binding protein.

Antibody variable domains include an amino acid sequence of an immunoglobulin light or heavy chain (modified as desired) that comprises the following amino acid regions, in sequence from N-terminal to C-terminal (unless otherwise indicated): FR1, CDR1, FR2, CDR2, FR3, CDR3, FR4. A "variable domain" includes an amino acid sequence capable of folding into a canonical domain (VH or VL) having a dual beta sheet structure wherein the beta sheets are connected by a disulfide bond between a residue of a first beta sheet and a second beta sheet.

Antibody complementarity determining regions ("CDR") include an amino acid sequence encoded by a nucleic acid sequence of an organism's immunoglobulin genes that normally (i.e., in a wild-type animal) appears between two framework regions in a variable region of a light or a heavy chain of an immunoglobulin molecule (for example, an antibody or a T cell receptor). A CDR can be encoded by, for example, a germline sequence or a rearranged or unrearranged sequence, and, for example, by a naive or a mature B cell or a T cell. In some circumstances (for example, for a CDR3), CDRs can be encoded by two or more sequences (for example, germline sequences) that are not contiguous (for example, in a nucleic acid sequence that has not been rearranged) but are contiguous in a B cell nucleic acid sequence, for example, as the result of splicing or connecting the sequences (for example, V-D-J recombination to form a heavy chain CDR3).

Each of the above components of antibodies can be produced according to the method of the present invention.

Bispecific antibodies include antibodies capable of selectively binding two or more epitopes. Bispecific antibodies generally comprise two different heavy chains, with each heavy chain specifically binding a different epitope, either on two different molecules (for example, antigens) or on the same molecule (for example, on the same antigen). If a bispecific antibody is capable of selectively binding two different epitopes (a first epitope and a second epitope), the affinity of the first heavy chain for the first epitope will generally be at least one to two, three or four orders of magnitude lower than the affinity of the first heavy chain for the second epitope, and vice versa. The epitopes recognized by the bispecific antibody can be on the same or a different target (for example, on the same or a different protein). Bispecific antibodies can be made, for example, by combining heavy chains that recognize different epitopes of the same antigen. For example, nucleic acid sequences encoding heavy chain variable sequences that recognize different epitopes of the same antigen can be fused to nucleic acid sequences encoding different heavy chain constant regions, and such sequences can be expressed in a cell that expresses an immunoglobulin light chain. A typical bispecific antibody has two heavy chains each having three heavy chain CDRs, followed by (N-terminal to C-terminal) a CH1 domain, a hinge, a CH2 domain, and a CH3 domain, and an immunoglobulin light chain that either does not confer antigen-binding specificity but that can associate with each heavy chain, or that can associate with each heavy chain and that can bind one or more of the epitopes bound by the heavy chain antigen-binding regions, or that can associate with each heavy chain and enable binding or one or both of the heavy chains to one or both epitopes, and can be produced according to the invention.

For example, for antibody embodiments, the present invention is amenable for research and production use for diagnostics and therapeutics based upon all major antibody classes, namely IgG, immunoglobulin A (IgA), immunoglobulin M (IgM), immunoglobulin D (IgD) and immunoglobulin E (IgE). IgG is a preferred class, such as IgG1 (including IgG1λ and IgG1κ), IgG2 and IgG4. Exemplary antibodies to be produced according to the present invention include Alirocumab, Atoltivimab, Maftivimab, Odesivimab, Odesivivmab-ebgn, Casirivimab, Imdevimab, Cemiplimab, Cemplimab-rwlc, Dupilumab, Evinacumab, Evinacumab-dgnb, Fasimumab, Nesvacumab, Trevogrumab, Rinucumab and Sarilumab.

In some exemplary embodiments, the protein in the microparticle formulation is an antibody, a human antibody, a humanized antibody, a chimeric antibody, a monoclonal antibody, a multispecific antibody, a bispecific antibody, an antigen-binding antibody fragment, a single chain antibody, a diabody, triabody or tetrabody, a dual-specific, tetravalent immunoglobulin G-like molecule, termed dual variable domain immunoglobulin (DVD-IG), an IgD antibody, an IgE antibody, an IgM antibody, an IgG antibody, an IgG1 antibody, an IgG2 antibody, an IgG3 antibody, or an IgG4 antibody. In some exemplary embodiments, the antibody is an IgG1 antibody. In some exemplary embodiments, the antibody is an IgG2 antibody. In still other exemplary embodiments, the antibody is an IgG4 antibody. In other exemplary embodiments, the antibody includes a chimeric hinge. In still other exemplary embodiments, the antibody includes a chimeric Fc. In other exemplary embodiments, the antibody is a chimeric IgG2/IgG4 antibody. In other exemplary embodiments, the antibody is a chimeric IgG2/IgG1 antibody. In some exemplary embodiments, the antibody is a chimeric IgG2/IgG1/IgG4 antibody.

In some exemplary embodiments, the antibody is selected from a group comprising an anti-Programmed Cell Death 1 (anti-PD1) antibody (for example, an anti-PD1 antibody as described in U.S. Pat. No. 9,987,500), an anti-Programmed Cell Death Ligand-1 (anti-PD-L1) antibody (for example, an anti-PD-L1 antibody as described in in U.S. Pat. No. 9,938,345), an anti-delta-like ligand 4 (anti-Dll4) antibody, an anti-Angiopoetin-2 (anti-ANG2) antibody (for example, an anti-ANG2 antibody as described in U.S. Pat. No. 9,402,898), an anti-Angiopoetin-Like 3 (anti-AngPtl3) antibody (for example, an anti-AngPtl3 antibody as described in U.S. Pat. No. 9,018,356), an anti-platelet derived growth factor receptor (anti-PDGFR) antibody (for example, an anti-PDGFR antibody as described in U.S. Pat. No. 9,265,827), an anti-Erb3 antibody, an anti-Prolactin Receptor antibody (for example, anti-PRLR antibody as described in U.S. Pat. No. 9,302,015), an anti-Complement antibody (for example, an anti-C5 antibody as described in U.S. Pat. No. 9,795,121), an anti-tumor necrosis factor (anti-TNF) antibody, an anti-epidermal growth factor receptor (anti-EGFR) antibody (for example, an anti-EGFR antibody as described in U.S. Pat. No. 9,132,192 or an anti-EGFRvIII antibody as described in U.S. Pat. No. 9,475,875), an anti-Proprotein Convertase Subtilisin Kexin-9 (anti-PCSK9) antibody (for example, an anti-PCSK9 antibody as described in U.S. Pat. No. 8,062,640 or U.S. Pat. No. 9,540,449), an anti-Growth and Differentiation Factor-8 (anti-GDF8) antibody (for example, an anti-GDF8 antibody, also known as anti-myostatin antibody, as described in U.S. Pat. No. 8,871,209 or U.S. Pat. No. 9,260,515), an anti-Glucagon Receptor (anti-GCGR) antibody (for example, anti-GCGR antibody as described in U.S. Pat. No. 9,587,029 or U.S. Pat. No. 9,657,099), an anti-VEGF antibody, an anti-IL1R antibody, an anti-interleukin 4 receptor (anti-IL4R) antibody (for example, an anti-IL4R antibody as described in U.S. Pat. Appln. Pub. No. US2014/0271681A1 or U.S. Pat. No. 8,735,095 or U.S. Pat. No. 8,945,559), an anti-interleukin 6 receptor (anti-IL6R) antibody (for example, an anti-IL6R antibody as described in U.S. Pat. Nos. 7,582,298, 8,043,617 or 9,173,880), an anti-IL1 antibody, an anti-IL2 antibody, an anti-IL3 antibody, an anti-IL4 antibody, an anti-IL5 antibody, an anti-IL6 antibody, an anti-IL7 antibody, an anti-interleukin 33 (for example, an anti-IL33 antibody as described in U.S. Pat. No. 9,453,072 or U.S. Pat. No. 9,637,535), an anti-Respiratory syncytial virus (anti-RSV) antibody (for example, an anti-RSV antibody as described in U.S. Pat. Nos. 9,447,173 and 10,125,188, and U.S. Pat. Appl. Pub. No. US2019/0031741A1), an anti-Cluster of differentiation 3 (anti-CD3) antibody (for example, an anti-CD3 antibody, as described in U.S. Pat. No. 9,657,102), an anti-Cluster of differentiation antibody (for example, an anti-CD20 antibody as described in U.S. Pat. No. 9,657,102 and US20150266966A1, and in U.S. Pat. No. 7,879,984), an anti-CD19 antibody, an anti-CD28 antibody, an anti-Cluster of Differentiation-48 antibody (for example, an anti-CD48 antibody as described in U.S. Pat. No. 9,228,014), an anti-Fel dl antibody (for example, as described in U.S. Pat. No. 9,079,948), a SARS-CoV-2 treatment (anti-SARS-CoV-2 antibodies casirivimab and imdevimab, sold under the trademark REGN-COV™), an anti-SARS-CoV-2 antibody, an anti-Middle East Respiratory Syndrome virus (anti-MERS) antibody (for example, an anti-MERS antibody as described in U.S. Pat. No. 9,718,872), an antibody cocktail against Ebola (REGN-EB3 comprising atoltivimab, maftivimab and odesivimab-ebgn (sold under the trademark INMAZEB®)), an anti-Ebola virus antibody (for example, as described in U.S. Pat. No. 9,771,414), an anti-Zika virus antibody, an anti-Lymphocyte Activation Gene 3 (anti-LAG3) antibody (for example, an anti-LAG3 antibody, or an anti-CD223 antibody), an anti-Nerve Growth Factor (anti-NGF) antibody (for example, an anti-NGF antibody as described in U.S. Pat. Appln. Pub. No. US2016/0017029 and U.S. Pat. Nos. 8,309,088 and 9,353,176), an anti-Activin A antibody, and an anti-Protein Y antibody.

In some exemplary embodiments, the bispecific antibody may be selected from a group comprising an anti-CD3×anti-CD20 bispecific antibody (as described in U.S. Pat. No. 9,657,102 and US20150266966A1), an anti-CD3×anti-Mucin 16 bispecific antibody (for example, an anti-CD3×anti-Muc16 bispecific antibody), and an anti-CD3×anti-Prostate-specific membrane antigen bispecific antibody (for example, an anti-CD3×anti-PSMA bispecific antibody).

In some exemplary embodiments, the protein may be selected from a group comprising abciximab, adalimumab, adalimumab-atto, ado-trastuzumab, aflibercept, alemtuzumab, alirocumab, atezolizumab, avelumab, basiliximab, belimumab, benralizumab, bevacizumab, bezlotoxumab, blinatumomab, brentuximab vedotin, brodalumab, brolucizumab, canakinumab, capromab pendetide, certolizumab pegol, cemiplimab, cetuximab, denosumab, dinutuximab, dupilumab, durvalumab, eculizumab, elotuzumab, emicizumab-kxwh, emtansinealirocumab, evinacumab, evolocumab, fasinumab, golimumab, guselkumab, ibritumomab tiuxetan, idarucizumab, infliximab, infliximab-abda, infliximab-dyyb, ipilimumab, ixekizumab, mepolizumab, necitumumab, nesvacumab, nivolumab, obiltoxaximab, obinutuzumab, ocrelizumab, ofatumumab, olaratumab, omalizumab, panitumumab, pembrolizumab, pertuzumab, ramucirumab, ranibizumab, raxibacumab, reslizumab, rinucumab, rituximab, sarilumab, secukinumab, siltuximab, tocilizumab, tocilizumab, trastuzumab, trevogrumab, ustekinumab, and vedolizumab.

Antibody derivatives and fragments are amenable for production according to the present invention, and include, but are not limited to: antibody fragments (for example, single chain variable fragment-Fc (ScFv-Fc), domain antibody-Fc (dAB-Fc), half antibodies), multispecifics (for example, IgG-ScFv, IgG-dab, ScFV-Fc-ScFV, tri-specific) and Fc-Fusion Proteins (for example, Fc-Fusion (N-terminal), Fc-fusion (C-terminal), mono Fc-fusion, bi-specific Fc-fusion). The phrase "Fc-containing protein" includes antibodies, bispecific antibodies, antibody derivatives containing an Fc, antibody fragments containing an Fc, Fc-fusion proteins, immunoadhesins, and other binding proteins that comprise at least a functional portion of an immunoglobulin CH2 and CH3 region. A "functional portion" refers to a CH2 and CH3 region that can bind a Fc receptor (for example, an FcγR; or an FcRn, (neonatal Fc receptor), and/or that can participate in the activation of complement. If the CH2 and CH3 region contains deletions, substitutions, and/or insertions or other modifications that render it unable to bind any Fc receptor and also unable to activate complement, the CH2 and CH3 region is not functional.

Antigen binding molecules (ABMs) and ABM conjugates having non-native formats, such as Fab domains in non-native configurations, can be expressed according to the present invention, and are disclosed in WO 2021/026409 A1. Multispecific binding molecules (MBMs) and MBM conjugates can be produced according to the present invention, and are disclosed in WO 2021/091953A1 and WO 2021/030680 A1.

Fc-containing proteins can comprise modifications in immunoglobulin domains, including where the modifications affect one or more effector function of the binding protein (for example, modifications that affect FcγR binding, FcRn binding and thus half-life, and/or CDC activity). Such modifications include, but are not limited to, the following modifications and combinations thereof, with reference to EU numbering of an immunoglobulin constant region: 238, 239, 248, 249, 250, 252, 254, 255, 256, 258, 265, 267, 268, 269, 270, 272, 276, 278, 280, 283, 285, 286, 289, 290, 292, 293, 294, 295, 296, 297, 298, 301, 303, 305, 307, 308, 309, 311, 312, 315, 318, 320, 322, 324, 326, 327, 328, 329, 330, 331, 332, 333, 334, 335, 337, 338, 339, 340, 342, 344, 356, 358, 359, 360, 361, 362, 373, 375, 376, 378, 380, 382, 383, 384, 386, 388, 389, 398, 414, 416, 419, 428, 430, 433, 434, 435, 437, 438, and 439.

For example, and not by way of limitation, the binding protein may be an Fc-containing protein and exhibit enhanced serum half-life (as compared with the same Fc-containing protein without the recited modification(s)) and have a modification at position 250 (for example, E or Q); 250 and 428 (for example, L or F); 252 (for example, L/Y/F/W or T), 254 (for example, S or T), and 256 (for example, S/R/Q/E/D or T); or a modification at 428 and/or 433 (for example, L/R/SI/P/Q or K) and/or 434 (for example, H/F or Y); or a modification at 250 and/or 428; or a modification at 307 or 308 (for example, 308F, V308F), and 434. In another example, the modification can comprise a 428L (for example, M428L) and 434S (for example, N434S) modification; a 428L, 2591 (for example, V259I), and a 308F (for example, V308F) modification; a 433K (for example, H433K) and a 434 (for example, 434Y) modification; a 252, 254, and 256 (for example, 252Y, 254T, and 256E) modification; a 250Q and 428L modification (for example, T250Q and M428L); a 307 and/or 308 modification (for example, 308F or 308P).

As stated above, the present invention is also amenable to the production of other molecules, including fusion proteins. These proteins can comprise part or all of two or more proteins, one of which is an Fc portion of an immunoglobulin molecule, that are not fused in their natural state. Fc-fusion proteins include Fc-Fusion (N-terminal), Fc-Fusion (C-terminal), Mono Fc-Fusion and Bi-specific Fc-Fusion. Preparation of fusion proteins comprising certain heterologous polypeptides fused to various portions of antibody-derived polypeptides (including the Fc domain) has been described, for example, by Ashkenazi et al., Proc. Natl. Acad. Sci USA 88: 10535-39 (1991); Byrn et al., Nature 344:677-70, 1990; and Hollenbaugh et al., "Construction of Immunoglobulin Fusion Proteins", in Current Protocols in Immunology, Suppl. 4, pages 10.19.1-10.19.11 (1992). Receptor Fc-containing proteins also are described in C. Huang, "Receptor-Fc fusion therapeutics, traps, and MFMETIBODY technology," 20(6) *Curr. Opin. Biotechnol.* 692-9 (2009).

Receptor Fc-fusion proteins comprise one or more of one or more extracellular domain(s) of a receptor coupled to an Fc moiety, which in some embodiments comprises a hinge region followed by a CH2 and CH3 domain of an immunoglobulin. In some embodiments, the Fc-fusion protein contains two or more distinct receptor chains that bind to a single or more than one ligand(s). Some receptor Fc-fusion proteins may contain ligand binding domains of multiple different receptors.

In some exemplary embodiments, the protein may be a recombinant protein that contains an Fc moiety and another domain, (for example, an Fc-fusion protein). In other exemplary embodiments, an Fc-fusion protein is a receptor Fc-fusion protein, which contains one or more extracellular domain(s) of a receptor coupled to an Fc moiety. In other exemplary embodiments, the Fc moiety includes a hinge region followed by a CH2 and CH3 domain of an IgG. In yet other exemplary embodiments, the receptor Fc-fusion protein contains two or more distinct receptor chains that bind to either a single ligand or multiple ligands.

For example, an Fc-fusion protein may be a Trap protein, such as for example an IL-1 trap (for example, rilonacept, which contains the IL-1 receptor accessory protein (RAcP) ligand binding region fused to the Il-1R1 extracellular region fused to Fc of human IgG1 (hIgG1); see, U.S. Pat. No. 6,927,004, which is herein incorporated by reference in its entirety), or a VEGF-Trap (for example, aflibercept or ziv-aflibercept, which comprises the Ig domain 2 of the VEGF receptor Flt1 fused to the Ig domain 3 of the VEGF receptor Flk1 fused to Fc of hIgG10). In other exemplary embodiments, an Fc-fusion protein may be a ScFv-Fc-fusion protein, which contains one or more antigen-binding domain(s), such as a variable heavy chain fragment and a variable light chain fragment, of an antibody coupled to an Fc moiety.

Mini-trap proteins are trap proteins that use a multimerizing component (MC) instead of a Fc portion, and are disclosed, for example, in U.S. Pat. Nos. 7,279,159 and 7,087,411, and can be produced according to the present invention.

In exemplary embodiments, the initial protein is in the form of a dry powder, for example a micronized, dry powder. In some exemplary embodiments, the protein is spray-dried powder (SDP). The use of spray-dried protein instead of a solution of protein has the advantages of higher protein loading in the microparticles and better protein stability during the encapsulation process.

In some exemplary embodiments, the dry protein molecules remain in solid state and surrounded by stabilizers or other excipients during the whole encapsulation process and storage conditions. Excipients in the protein powder may include any excipient known to improve protein stability during storage, for example, sorbitol, glycerol, mannitol, trehalose, sucrose, arginine, alanine, proline, glycine, leucine, histidine, sodium chloride, polysorbate 20, polysorbate 80, polyethylene glycol, or phosphate buffer.

In exemplary embodiments, the encapsulated spray-dried protein exhibits high recovery and low aggregation, possibly due to minimized surface interaction as only a small portion of surface proteins are exposed to the interface. In yet other exemplary embodiments, the protein is micronized prior to encapsulation.

Hydrogel Microparticles (Microgels)

In other exemplary embodiments, pharmaceutical compositions produced using the disclosed non-aqueous emulsion systems are provided. In other exemplary embodiments, the pharmaceutical composition comprises microgels that have a polymer cortex and micronized protein core. In yet other exemplary embodiments, the microgel comprises microparticles that are roughly spherical in shape.

Some microparticles and protein cores will approach sphericity, while others will be more irregular in shape. Thus, as used herein, the term "diameter" means each and any of the following: (a) the diameter of a sphere which circumscribes the microparticle or protein core, (b) the diameter of the largest sphere that fits within the confines of the microparticle or the protein core, (c) any measure between the circumscribed sphere of (a) and the confined sphere of (b), including the mean between the two, (d) the length of the longest axis of the microparticle or protein core, (e) the length of the shortest axis of the microparticle or protein core, (f) any measure between the length of the long axis (d) and the length of the short axis (e), including the mean between the two, and/or (g) equivalent circular diameter (ECD), as determined by micro-flow imaging (MFI), nanoparticle tracking analysis (NTA), or as volume or number averaged diameter by light scattering methods such as static light scattering (SLS), dynamic light scattering (DLS), or laser diffraction analysis. Diameter is generally expressed in micrometers (km or micron). Diameter can be determined by optical measurement or scanning electron microscopy measurement.

Microparticles produced by the disclosed non-aqueous emulsion methods include multiple molecules of protein with low, very low, or close to zero amounts of water (for example, less than 3% water by weight). In some exemplary embodiments, a micronized protein particle may have an ECD ranging from 2 microns to about 35 microns, or from 2.0 to 50 μm, or 5.0 to 15.0 μm, or about 10 μm. The micronized protein particle is not limited to any particular protein entity, and is suited to the preparation and delivery of a therapeutic protein including the proteins described above.

For example, the protein particle may be micronized by spray-drying, lyophilization and milling, jet milling, reversible precipitation in non-solvent, granulation, gradual precipitation (see U.S. Pat. No. 7,998,477), supercritical fluid precipitation (see U.S. Pat. No. 6,063,910), or high-pressure carbon dioxide induced particle formation (Bustami et al., Pharma. Res. 17: 1360-66 (2000)). As used herein, the phrase "spray-dry" refers to a method of producing a dry powder containing micron-sized particles from a slurry or suspension by using a spray-dryer. Spray-dryers employ an atomizer or spray nozzle to disperse the suspension or slurry into a controlled drop size spray.

Drop sizes from 10 μm to 500 μm can be generated by spray-drying. As the solvent (water or organic solvent) dries, the protein substance dries into a micron-sized particle, forming a powder-like substance; or in the case of a protein-polymer suspension, during drying, the polymer hardened shell around the protein load.

In some exemplary embodiments, a concentration of micronized protein powder suspended in a dispersed phase suspension, for example a dispersed phase comprising a hydrocarbon solution, is between about 1% and about 50% w/v, between about 1% and about 30% w/v, between about 1% and about 20% w/v, between about 1% and about 10% w/v, between about 1% and about 5% w/v, between about 5% and about 30% w/v, between about 5% and about 20% w/v, between about 5% and about 10% w/v, about 1% w/v, about 2% w/v, about 3% w/v, about 4% w/v, about 5% w/v, about 6% w/v, about 7% w/v, about 8% w/v, about 9% w/v, about 10% w/v, about 15% w/v, about 20% w/v, about 25% w/v, about 30% w/v, about 35% w/v, about 40% w/v, about 45% w/v, or about 50% w/v.

In some embodiments, the micronized protein is a VEGF-Trap protein. Pharmaceutical formulations for the formation of micronized VEGF-Trap protein particles may contain from about 10 mg/mL to about 100 mg/mL VEGF-Trap protein, about 1.0 to about 50 mg/mL protein, about 10 mg/mL, about 15 mg/mL, about 20 mg/mL, about 25 mg/mL, about 30 mg/mL, about 35 mg/mL, about 40 mg/mL, about 45 mg/mL, about 50 mg/mL, about 55 mg/mL, about 60 mg/mL, about 65 mg/mL, about 70 mg/mL, about 75 mg/mL, about 80 mg/mL, about 85 mg/mL, about 90 mg/mL, about 95 mg/mL, or about 100 mg/mL VEGF Trap protein. In some exemplary embodiments, the VEGF-Trap protein may be an ophthalmic formulation suitable for intravitreal administration to the eye, substantially like the formulations disclosed in U.S. Pat. No. 8,092,803, which is incorporated by reference into this application.

In exemplary embodiments, the microparticles produced using the disclosed non-aqueous emulsion systems may have a range of diameters of from about 1 μm to about 200 m about 1 μm to about 150 μm, about 1 μm to about 100 μm, about 2 μm to about 70 μm, about 5 μm to about 65 μm, about 10 μm to about 60 μm, about 15 μm to about 55 μm, about 10 am to about 50 μm, about 1.0 μm to 15 μm, about 20 μm, about 25 μm, or about 30 μm, about. The size variation in large part reflects the thickness of the polymer cortex, although the diameter of the protein core could contribute to size variation to some extent.

In some exemplary embodiments, the microparticles formed by the disclosed non-aqueous emulsion methods are flowable microparticle compositions. The disclosed, flowable microparticle compositions can be suspended with pharmaceutically acceptable excipients in a pharmaceutically acceptable formulation, for example in a formulation comprising pH buffered saline, an aqueous solution or a non-aqueous solution.

The term "excipient" includes any non-therapeutic agent added to a pharmaceutical composition to provide a desired consistency or stabilizing effect. Suitable pharmaceutical excipients include, for example, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The flowable microparticle compositions can be administered parenterally, for example using a syringe such as a syringe with a 27G needle. The microparticles are useful in the time-release or extended release of protein therapeutics.

The term "formulation" includes any combination of a drug or therapeutic agent, for example the microparticles of the present invention, and any additional components, excipients, or vehicles which may be useful in the application of a therapeutic agent. In some exemplary embodiments, a formulation may include microparticles and pH buffered saline, aqueous solution, or non-aqueous solution. In some exemplary embodiments, the microparticle formulations are injected intravitreally, suprachoroidally, or subcutaneously. For example, it is envisioned that the VEGF-Trap microparticles are useful in the extended or sustained release of VEGF-Trap therapeutic protein in, for example, the vitreous for the treatment of vascular eye disorders, or subcutaneous implantation for the extended or sustained release of VEGF-Trap to treat other disorders.

The microparticles in accordance with the present disclosure release protein in a physiological aqueous environment at about 37° C. at a relatively constant rate over an extended period of time, to at least 60, 90, 120, or 150 days (sustained release).

In some exemplary embodiments, compositions containing microparticles produced using the non-aqueous emulsion methods disclosed herein are provided, wherein the composition comprises greater than 100 mg of spray-dried protein. In some exemplary embodiments, the non-aqueous emulsion methods have greater than 90% yield, and produce microparticles with a purity of greater than 99% and that have greater than 10% w/w loading, and greater than 10% burst for a 50-100 μL injection volume.

Pharmaceutical formulations including microparticles prepared in accordance with the present disclosure may be contained within any container suitable for storage of medicines and other therapeutic compositions. For example, exemplary pharmaceutical formulations may be contained within a sealed and sterilized plastic or glass container having a defined volume such as a vial, ampule, syringe, cartridge, or bottle. Different types of vials can be used to contain the formulations of the present disclosure including, for example, clear and opaque (e.g., amber) glass or plastic vials. Likewise, any type of syringe can be used to contain or administer the pharmaceutical formulations of the present disclosure.

Pharmaceutical formulations including microparticles prepared in accordance with the present disclosure may be contained within "normal tungsten" syringes or "low tungsten" syringes. As will be appreciated by persons of ordinary skill in the art, the process of making glass syringes generally involves the use of a hot tungsten rod which functions to pierce the glass, thereby creating a hole from which liquids can be drawn and expelled from the syringe. This process results in the deposition of trace amounts of tungsten on the interior surface of the syringe. Subsequent washing and other processing steps can be used to reduce the amount of tungsten in the syringe. As used herein, the term "normal tungsten" means that the syringe contains greater than or equal to 500 parts per billion (ppb) of tungsten. The term "low tungsten" means that the syringe contains less than 500 ppb of tungsten. For example, a low tungsten syringe, according to the present disclosure, can contain less than about 490, 480, 470, 460, 450, 440, 430, 420, 410, 390, 350, 300, 250, 200, 150, 100, 90, 80, 70, 60, 50, 40, 30, 20, 10 or fewer ppb of tungsten.

The rubber plungers used in syringes, and the rubber stoppers used to close the openings of vials, may be coated to prevent contamination of the medicinal contents of the syringe or vial, or to preserve their stability. Thus, pharmaceutical formulations of the present disclosure, according to certain embodiments, may be contained within a syringe that comprises a coated plunger, or within a vial that is sealed with a coated rubber stopper. For example, the plunger or stopper may be coated with a fluorocarbon film. Examples of coated stoppers or plungers suitable for use with vials and syringes containing the pharmaceutical formulations of the present disclosure are mentioned in, for example, U.S. Pat. Nos. 4,997,423; 5,908,686; 6,286,699; 6,645,635; and 7,226,554, the contents of which are incorporated by reference herein in their entireties.

Exemplary coated rubber stoppers and plungers that can be used in the context of the present disclosure are commercially available under the tradename "FluoroTec®", available from West Pharmaceutical Services, Inc. (Lionville, Pa.). FluoroTec® is an example of a fluorocarbon coating used to minimize or prevent drug product from adhering to the rubber surfaces.

Exemplary pharmaceutical formulations may be contained within a low tungsten syringe that comprises a fluorocarbon-coated plunger.

Exemplary pharmaceutical formulations can be administered to a patient by parenteral routes such as injection (for example, subcutaneous, intravenous, intramuscular, intraperitoneal, etc.) or percutaneous, mucosal, nasal, pulmonary or oral administration. Numerous reusable pen or autoinjector delivery devices can be used to subcutaneously deliver the pharmaceutical formulations of the present disclosure. Examples include, but are not limited to, delivery devices sold under the trademarks Autopen® (Owen Mumford, Inc., Woodstock, UK), Disetronic PenFine® Pen (Disetronic Medical Systems, Bergdorf, Switzerland), Humalog® Mix75/25® pen, Humalog® pen, Humulin® 70/30 pen (Eli Lilly and Co., Indianapolis, Ind.), NovoPen® I, II and III (Novo Nordisk, Copenhagen, Denmark), NovoPen® Junior (Novo Nordisk, Copenhagen, Denmark), BD™ pen (Becton Dickinson, Franklin Lakes, N.J.), OptiPen®, OptiPen Pro®, and OptiPen Starlet™, and OptiClik® (Sanofi-Aventis, Frankfurt, Germany).

Examples of disposable pen or autoinjector delivery devices having applications in subcutaneous delivery of a pharmaceutical composition of the present disclosure include, but are not limited to, delivery devices sold under the trademarks the SoloSTAR® pen (Sanofi-Aventis), the FlexPen® (Novo Nordisk), and the KwikPen™ (Eli Lilly), the SureClick™ Autoinjector (Amgen, Thousand Oaks, Calif.), the Pelet® (Haselmeier, Stuttgart, Germany), the EpiPen® (Dey, L. P.), and the Humira® Pen (Abbott Labs, Abbott Park, Ill.).

The use of a microinfusor to deliver pharmaceutical formulations including microparticles prepared in accordance with the present disclosure is also contemplated herein. As used herein, the term "microinfusor" means a subcutaneous delivery device designed to slowly administer large volumes (for example, up to about 2.5 mL or more) of a therapeutic formulation over a prolonged period of time (for example about 10, 15, 20, 25, 30 or more minutes). See, for example, U.S. Pat. Nos. 6,629,949; 6,659,982; and Meehan et al., *J. Controlled Release* 46:107-116 (1996). Microinfusors are particularly useful for the delivery of large doses of therapeutic proteins contained within high concentration (for example, about 100, 125, 150, 175, 200 or more mg/mL) or viscous solutions.

EXAMPLES

The following non-limiting examples are intended to illustrate synthesis of blank microgels, drug microgels, formulations containing drug microgels, and methods of making drug microgels using non-aqueous emulsion systems. Table 1 includes materials used in the following examples. In an exemplary embodiment, a solid composition of spray-dried fluorescently labelled VEGF-Trap comprises 69.8% w/w VEGF-Trap, 0.7% w/w Alexa Fluor™ 488-labelled VEGF-Trap, 13.1% w/w glycosylation on VEGF-Trap, 2.1% w/w sodium phosphate, 14.1% w/w sucrose, and 0.2% w/w polysorbate (PS) 80. It should be understood that the concentrations of excipients in a spray-dried powder may vary without impacting the effectiveness of the method of the present invention, and that the method of the present invention may be used with a spray-dried powder comprising any protein with any combination of excipients.

TABLE 1

Materials for hydrogel microparticle fabrication

| Material | Description | Manufacture | Lot/Item # |
|---|---|---|---|
| Spray-Dried Fluorescently labelled Alexa-488 VEGF-Trap | 69.3 w/w % VEGF-Trap and 0.7 w/w % Alexa Fluor ™ 488-labeled VEGF-Trap | FDG, Regeneron, Tarrytown | N/A |
| HGEO-150 PA | 8-arm NH-PEG, 14450 MW [Hexaglycerolocta(aminopropyl) polyoxyethylene] | NOF Group | M147604 |
| HGEO-400 GS | 8-arm NHS-PEG, glutaryl, 45573 MW [Hexaglycerolocta(succinimidyloxy-glutaryl)polyoxyethylene] | NOF Group | M83620 |
| Dichloromethane | organic solvent | Sigma Aldrich | 270997-1L |
| PEG 1000 | Poly(ethylene glycol), 1000 | Sigma Aldrich | 8.07488 |
| PEG 2000 | Poly(ethylene glycol) BioUltra, 2,000 | Sigma Aldrich | 84797-250G-F |
| PEG 8000 | BioUltra, for molecular biology, 8,000 | Sigma Aldrich | 81268 |
| PEG 20 k | BioUltra, 20,000 | Sigma Aldrich | 95172-250G-F |
| FC-40 | Fluorinert ™ FC-40 | Sigma Aldrich | F9755 |
| FC-70 | Fluorinert ™ FC-70 | Sigma Aldrich | F9880 |
| Pico Surf 1 | Fluorosurfactant | Sphere Fluidics | C014 |

Example 1: Synthesis of Blank Crosslinked PEG Microgels Using Non-Aqueous Emulsion Systems Synthesis of blank crosslinked PEG microgels via H/F bulk emulsion, a non-aqueous emulsion system, as illustrated in FIG. 1A, may be carried out by mixing a stock solution of NHS:NH:PEG8k including 40 kDa PEG-NHS 32% w/v in dichloromethane (DCM), PEG-NH 12% w/v in DCM and 8 kDa (non-functionalized linear) PEG 35% w/v in DCM in a ratio of 20 µL:20 µL:260 µL in a 1.5 mL microtube. The contents of the 1.5 mL microtube may then be transferred quickly to 6 mL FC-40 containing 0.5% w/w fluorosurfactant, Pico Surf™ 1. The DCM in FC-40 solution may then be emulsified through vortexing or homogenizing. The crosslinking reaction continues and completes in individual droplets, and emulsion droplets finally harden into PEG microgels after removal of DCM.

Upon collecting the blank crosslinked PEG microgels, large polymer aggregates may form and precipitate out from the emulsion. Smaller droplets may remain in shape while larger droplets (about >10 µm) tend to flocculate and merge together before the crosslinking reaction is completed and microgels hardened.

To prevent flocculation and subsequent aggregation of the microgels, a more viscous continuous phase can be used to replace the FC-40 in the protocol described above. According to Stoke's Law, it is known that one way to reduce the phase separation rate is to increase the viscosity of continuous phase. Therefore, another commercially available fluorocarbon, Fluoriner™ FC-70 (perfluorotripentylamine), with much higher viscosity, 24 cP (as compared to FC-40, having 4.1 cP) can be used for microgel fabrication. The use of more viscous fluorocarbon led to less aggregation and successful formation of microgels (data not shown).

Example 2. Optimizing Gelation Rate Using a Cross-Linking Modulator

As described in Example 1, crosslinking may be achieved through mixing a precursor containing nucleophilic groups (PEG-NH) with a precursor containing electrophilic groups (PEG-NHS). As the reaction will start immediately upon mixing, the reaction rate should be suppressed to allow enough time for the subsequent emulsification process. The inventors found that the reaction of 15 kDa PEG-NHS and 40 k Da PEG-NH upon mixing is concentration-dependent. The gelation speed was very fast at high PEG concentrations, and the reaction mixture may no longer be able to be micronized shortly after mixing. Diluting the polymer concentration reduces the rate of cross-linking. However, it also lowers the viscosity of the dispersed phase, which may lead to formation of smaller microgels that are less efficient in encapsulating spray-dried protein (SDP).

Therefore, exemplary embodiments of the method of the present invention include controlling the crosslinking reaction rate while keeping the viscosity of the dispersed phase high enough to generate larger droplets during emulsification, thereby producing larger microgels and ensuring efficient protein encapsulation. In some exemplary embodiments, the desired balance in properties are achieved by optimizing the amount of cross-linking modulator. In some exemplary embodiments, the cross-linking modulator is a linear, non-functionalized PEG, which may be added to the reaction mixture to maintain the hydrocarbon phase viscosity while reducing the functionalized PEG precursor concentration.

To optimize a ratio of functionalized precursor to pure non-functionalized cross-linking modulator, experiments were performed to evaluate gelation speed, providing sufficient data points to extrapolate our findings. First, the following stock solutions were prepared: 40 kDa PEG-NHS 32% w/v in DCM, PEG-NH 12% w/v in DCM, and 8 kDa (non-functionalized linear) PEG 35% w/v in DCM. A PEG-NH and 8 kDa PEG solution was then mixed in a 1.5 mL Eppendorf microtube by vortexing. Finally, various PEG-NHS solutions were added to make 300 µL mixtures. After vortexing to homogenize the mixture and start the reaction, the microtube was constantly tilted to check if the mixture stopped flowing, which would indicate that the gel is formed. The gelation times for various ratios of PEG-NHS:PEG-NH:PEG 8 kDa are shown in Table 2.

As illustrated in Table 2 below, decreasing the functionalized crosslinkable polymer or polymer precursor concentration and replacing functionalized crosslinkable polymer or polymer precursor with the cross-linking modulator (pure non-functionalized linear PEG chains) can extend the gelation time to allow for the subsequent emulsification process.

TABLE 2

Varying PEG precursors and non-functionalized PEG to optimize gelation time

| PEG-NHS:PEG-NH:PEG 8k (v:v:v µL) | Approximate Gelation Time |
| --- | --- |
| 150:150:0 | <1 second, immediately upon mixing |
| 100:100:100 | <1 second, immediately upon mixing |
| 50:50:200 | Within 5 seconds after mixing |
| 30:30:240 | Gelation in about 10-20 seconds |
| 20:20:260 | Gelation gradually in >300 seconds |

Example 3. Encapsulation of Spray-Dried Protein in Crosslinked PEG Microgels

In some exemplary embodiments, encapsulation of spray-dried protein in crosslinked PEG microgels may be achieved as illustrated in FIG. 3. Production of microgels was carried out by first preparing a stock solution of 20 kDa PEG 35% w/v in DCM, HGEO-400GS (PEG-NHS) 32% w/v in DCM, and HGEO-150PA (PEG-NH) 12% w/v in DCM. 260 μL 20 kDa PEG and 20 μL PEG-NH were then mixed into a solution before adding 10 mg micronized protein powder (for example, VEGF-Trap SDP) in a 1.5 mL microtube, vortexing, and sonicating for 10 minutes to make a suspension. 20 μL of PEG-NHS was then added to the suspension before vortexing to homogenize. The contents of the 1.5 mL microtube were then added to 6 mL of Fluorinert™ FC-70 containing 0.5% w/w PS-1. The mixture was then emulsified through vortexing or homogenization. The emulsion was placed under vacuum with gentle stirring for over 3 hours to complete the crosslinking reaction and remove the DCM. The microgels were then vacuum filtered and washed through a 0.45 μm polyethersulfone (PES) membrane. Vacuum filtration may be used to further dry the microgels as needed before final collection. The products were further dried under vacuum for an extended period to reduce the residual solvents.

The powder of microgels fabricated through the procedure above can be suspended and dispersed easily in phosphate buffered saline (PBS) containing a surfactant like 0.1% PVA, or suspended in a non-aqueous liquid vehicle such as medium chain triglycerides. To identify and visualize the location of loaded protein particles, VEGF-Trap (for example, aflibercept) may be labelled with Alexa Fluor™ 488 tetrafluorophenyl (TFP) ester dye through non-specific conjugation. The VEGF-Trap containing 1% Alexa Fluor™ 488-labelled protein may then be spray-dried into SDP so that the SDP particles are visible using fluorescence microscopy.

Crosslinked PEG microgels encapsulating SDP particles comprising fluorescently labeled VEGF-Trap were produced as described above and suspended in a PBS buffer containing 0.1% PVA, a surfactant used to prevent aggregation and promote dispersion in aqueous solution, or in FC-70, and imaged under a microscope.

FIGS. 4A and 4B show bright-field and fluorescence microscope images of the SDP-loaded microgels re-suspended in FC-70. A distribution of microgels from 15 μm to 60 μm in size with an average size of about 26 μm was observed (through image analysis using Leica LAS X software), while a population of fine particles (<5 μm) was also seen. The fluorescent signal from SDP collocated well with the particle images in the bright-field channel, confirming the effective encapsulation of SDP particles in the microgel. Higher magnification images as shown in FIGS. 5A and 5B show that the microgels were nearly spherical, with SDP particles (size 2-5 μm) evenly distributed inside the microgels. The SDP particles in the microgels maintained their original raisin-like shapes, which indicates that the whole encapsulation process according to the method of the present invention has minimum impact on the integrity of SDP particles.

FIGS. 6A, 6B and 7 show bright-field and fluorescent microscope images of the crosslinked PEG microgels suspended in PBS. These images demonstrate that although PEG is water soluble, the crosslinked PEG microgels maintained their spherical structure in the aqueous buffer without being disassembled, indicating successful crosslinking of PEG precursors and formation of microgels. Fluorescent signals from the SDP collocated with the microgel particles, which suggested that, although the PEG matrix possibly became swollen by the water of the aqueous buffer, proteins were still retained within the microgel. These results suggested that the obtained crosslinked PEG microgels encapsulating VEGF-Trap have properties needed for potential sustained release applications.

While in the foregoing specification aspects of the present technologies have been described in relation to certain embodiments thereof, and many details have been put forth for the purpose of illustration, it will be apparent to those skilled in the art that the concepts and principles disclosed herein may be extended to additional embodiments and that certain of the details described herein can be varied considerably without departing from the basic principles of the disclosure.

All references cited herein, including U.S. patent and applications are incorporated by reference in their entirety. The present disclosure may be embodied in other specific forms without departing from the spirit or essential attributes thereof and, accordingly, reference should be made to the appended claims, rather than to the foregoing specification, as indicating the scope of the disclosure.

What is claimed is:

1. A method of producing microparticles comprising:

(a) combining a polyethylene glycol-amine polymer, a polyethylene glycol-N-hydroxysuccinimide polymer, a polyethylene glycol (PEG) polymer, and a powder including a vascular endothelial growth factor-Trap (VEGF-Trap) protein with dichloromethane to form a dispersed phase suspension;

(b) adding said dispersed phase suspension to a continuous phase solution, wherein said continuous phase solution includes perfluorotripentylamine and a triblock copolymer perfluoropolyether-b-polyethylene glycol-b-perfluoropolyether (PFPE-PEG-PFPE), to form a combined dispersed phase suspension and continuous phase solution;

(c) applying blending forces to said combined dispersed phase suspension and continuous phase solution to form a non-aqueous emulsion having multiple dichloromethane droplets including said polyethylene glycol-amine polymer, said polyethylene glycol-N-hydroxysuccinimide polymer and said powder including VEGF-Trap in the perfluorotripentylamine; and (d) removing the dichloromethane and the perfluorotripentylamine from said non-aqueous emulsion to form isolated microparticles.

2. The method of claim 1, wherein the molar ratio of said amine to said N-hydroxysuccinimide is between 1:1 and 1:2.

3. The method of claim 1, wherein said polyethylene glycol-amine polymer and/or said polyethylene glycol-N-hydroxysuccinimide polymer is a 4-armed or an 8-armed compound.

4. The method of claim 1, wherein said VEGF-Trap protein is a truncated form of VEGF-Trap protein.

5. The method of claim 1, wherein said VEGF-Trap protein is aflibercept.

6. The method of claim 1, wherein said isolated microparticles have a diameter between 1·m and 200·m as measured by imaging analysis.

7. The method of claim 1, wherein said powder including a VEGF-Trap protein is micronized by spray-drying, electrospray drying, reversible precipitation, spray freezing, microtemplating, or a combination thereof.

8. The method of claim 1, wherein said blending forces comprise homogenization, vortexing, sonication, cavitation, agitation, or a combination thereof.

9. The method of claim 1, wherein said microparticles are sustained release microparticles.

10. The method of claim 1, wherein a concentration of said powder including a VEGF-Trap protein in said dispersed phase suspension is between 1.0% and 30% w/v.

11. The method of claim 1, wherein a total concentration of said polyethylene glycol-amine polymer and said polyethylene glycol-N-hydroxysuccinimide polymer in said dispersed phase suspension is between 5.0% and 35% w/v.

12. The method of claim 1, wherein a concentration of said PFPE-PEG-PFPE in said continuous phase solution is between 0.1% and 5.0% w/v.

13. The method of claim 1, further comprising suspending said isolated microparticles in a pharmaceutically acceptable formulation.

14. The method of claim 13, wherein said formulation comprises pH buffered saline, an aqueous solution, or a non-aqueous solution.

15. The method of claim 1, wherein said powder including a VEGF-Trap protein further comprises at least one excipient.

16. A microparticle made by the method of claim 1.

17. The method of claim 1, wherein a concentration of said PEG polymer in said dispersed phase suspension is between 5.0% and 35% w/v.

* * * * *